(12) United States Patent
Habash

(10) Patent No.: US 10,064,852 B2
(45) Date of Patent: *Sep. 4, 2018

(54) DECREASING EXPRESSION LEVEL OF APOPTOSIS-RELATED GENES BY TREATING A HUMAN SUBJECT WITH A NITROXIDE

(71) Applicant: Louis Habash, Irvine, CA (US)

(72) Inventor: Louis Habash, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/410,693

(22) Filed: Jan. 19, 2017

(65) Prior Publication Data

US 2017/0326122 A1    Nov. 16, 2017

Related U.S. Application Data

(63) Continuation-in-part of application No. 15/156,185, filed on May 16, 2016, now Pat. No. 9,579,311.

(51) Int. Cl.
*A01N 43/40* (2006.01)
*A61K 31/445* (2006.01)

(52) U.S. Cl.
CPC .................. *A61K 31/445* (2013.01)

(58) Field of Classification Search
CPC ................................................. A61K 31/445
USPC ........................................................ 514/315
See application file for complete search history.

(56) References Cited

U.S. PATENT DOCUMENTS 9,579,311 B1 * 2/2017 Habash ................ A61K 31/445
2009/0042937 A1 2/2009 Habash et al.

FOREIGN PATENT DOCUMENTS

WO    WO 2015/121317    8/2015

OTHER PUBLICATIONS

Abdul-Ghani, Mohammad, et al., "Rehabilitation of a Contract Killer: Caspase-3 Directs Stem Cell Differentiation," *Cell Stem Cell* (2008) 2(6):515-16.
Agosto, Mariela, et al., "Serum Caspase-3 p17 Fragment is Elevated in Patients With ST-Segment Elevation Myocardial Infarction: A Novel Observation," *J. Am. Coll. Cardiol.* (2011) 57(2): 220-221.
Ahmad, Manzoor, et al., "CRADD, a Novel Human ApoptoticAdaptor Moleculefor Caspase-2,and FasL/Tumor Necrosis Factor Receptor-interacting Protein RIP," *Cancer Res.* (1997) 57:615-19.
Amptoulach, Sousana, et al., "Expression of caspase-3 predicts prognosis in advanced noncardia gastric cancer," *Med Oncol.* (2015) 32(1):416.
Bender, LM, et al., "The adaptor protein TRADD activates distinct mechanisms of apoptosis from the nucleus and the cytoplasm," *Cell Death Differ.* (2005) 12(5):473-81.

Berindan-Neagoe, Ioana, et al., "Early Apoptosis Signals Induced by a Low Dose of Epigallocatechin 3-Gallate Interfere with Apoptotic and Cell Death Pathways," *J. Nanosci. Nanotech.* (2012) 12:2113-19.
Bodyak, Natalya, et al., "Gene expression profiling of the aging mouse cardiac myocytes," *Nucleic Acids Res.*, 2002, 30:3788-3794.
Boldin, Mark P., et al., "Involvement of MACH, a Novel MORT1/FADD-Interacting Protease, in Fas/APO-1- and TNF Receptor—Induced Cell Death," *Cell* (1996) 85(6): 803-15.
Bouchier-Hayes, Lisa, "The role of caspase-2 in stress-induced apoptosis," *J. Cell Mol. Med.* (2010) 14(6a):1212-24.
Cano, Carla E., et al., "Tumor Protein 53—Induced Nuclear Protein 1 is a Major Mediator of p53 Antioxidant Function," *Cancer Res.* (2009) 69:219-26.
Cartron, Pierre-François, et al., "Metaxins 1 and 2, two proteins of the mitochondrial protein sorting and assembly machinery, are essential for Bak activation during TNF alpha triggered apoptosis," *Cell. Signal.* (2014) 26(9):1928-34.
Chen, Chun-Hua, et al., "The Involvement of Programmed Cell Death 5 (PDCD5) in the Regulation of Apoptosis in Cerebral Ischemia/Reperfusion Injury," *CNS Neurosci. Ther.* (2013) 19(8): 566-576.
Cheng, Ai-xin, et al., "Expression of PDCD5, a novel apoptosis related protein, in human osteoarthritic cartilage," *Acta. Pharmacol. Sin.* (2004) 25(5): 685-90.
Cicala, Claudia, et al., "HIV-1 envelope induces activation of caspase-3 and cleavage of focal adhesion kinase in primal-3T human CD4+ T cells," *Proc. Nat'l Acad. Sci.* (2000) 97(3):1178-83.
Cooper, Dawn M., "The Balance between Life and Death: Defining a Role for Apoptosis in Aging," *J. Clin. Exp. Pathol.*, 2012, S4.
Cullen, SP, et al., "Caspase activation pathways: some recent progress," *Cell Death Differ.* (2009) 16:935-38.
De Magalhães, João Pedro, et al., "Meta-analysis of age-related gene expression profiles identifies common signatures of aging," *Bioinformatics*, 2009, 25:875-881.
Duan, Hangjun, et al., "RAIDD is a new 'death' adaptor molecule," *Nature* (1997) 385:86-89.
Duckett, Colin S., et al., "CD30-dependent degradation of TRAF2:implications for negative regulation of TRAF signaling and the control of cell survival," *Genes Dev.* (1997) 11(21): 2810-21.
Duckworth, Carrie A., et al., "Suppression of Apoptosis, Crypt Hyperplasia, and Altered Differentiation in the Colonic Epithelia of Bak-Null Mice," *Gastroenterol.* (2009) 136(3):943-52.
Edwards, Michael G., et al., "Gene expression profiling of aging reveals activation of a p53-mediated transcriptional program," *BMC Genomics*, 2007, 8:80.
Elner, Susan G., et al., "Human RPE Cell Apoptosis Induced by Activated Monocytes is Mediated by Caspase-3 Activation," *Trans. Am. Ophthalmol. Soc.* (2003) 101:77-91.

(Continued)

*Primary Examiner* — Nizal S Chandrakumar
(74) *Attorney, Agent, or Firm* — Knobbe, Martens, Olson & Bear, LLP

(57) ABSTRACT

Disclosed herein are methods for treating a human subject having a disease associated with an increased level of apoptosis using a nitroxide. Further disclosed are methods for treating a human subject in need of a reduced expression level of a gene associated with the apoptosis pathway using a nitroxide.

30 Claims, No Drawings

(56) References Cited

OTHER PUBLICATIONS

Ermolaeva, Maria A., et al., "Function of TRADD in tumor necrosis factor receptor 1 signaling and in TRIF-dependent inflammatory responses," *Nature Immunol.* (2008) 9:1037-46.

Fastje, Cynthia D., et al., "Exposure to sodium tungstate and Respiratory Syncytial Virus results in hematological/immunological disease in C57BL/6J mice," *Chem. Biol. Interact.* (2012) 196(3): 89-95.

Gervais, François G., et al., "Involvement of Caspases in Proteolytic Cleavage of Alzheimer's Amyloid-Bβ Precursor Protein and Amyloidogenic Aβ Peptide Formation," *Cell* (1999) 97(3):395-406.

Giebel, Jürgen, et al., "Age-related differential expression of apoptosis-related genes in conjunctival epithelial cells," *Acta Ophthalmol. Scand.* (2005) 83: 471-76.

Gironella, Meritxell, et al., "Tumor protein 53-induced nuclear protein 1 expression is repressed by miR-155, and its restoration inhibits pancreatic tumor development," *Proc. Nat'l Acad. Sci.* (2007) 104(41):16170-5.

Glass, Daniel, et al., "Gene expression changes with age in skin, adipose tissue, blood and brain," Genome Biol., 2013, 14:R75.

Gommeaux, Julien, et al., "Colitis and Colitis-Associated Cancer are Exacerbated in Mice Deficient for Tumor Protein 53-Induced Nuclear Protein 1," *Mol. Cell. Biol.* (2007) 27(6): 2215-2228.

Hermel, E., et al., "Specific caspase interactions and amplification are involved in selective neuronal vulnerability in Huntington's disease," *Cell Death Differ.* (2004) 11(4): 424-38.

Hsu, Hailing, et al., "TNF-Dependent Recruitment of the Protein Kinase RIP to the TNF Receptor-1 Signaling Complex," *Immunity* (1996) 4(4): 387-96.

Isaian, Anna, et al., "BAK, BAX, and NBK/BIK Proapoptotic Gene Alterations in Iranian Patients with Ataxia Telangiectasia," *J. of Clin. Immunol.* (2010) 30(1):132-7.

Jang, Young Mok, et al., "Doxorubicin treatment in vivo activates caspase-12 mediated cardiac apoptosis in both male and female rats," *FEBS Lett.* (2004) 577(3): 483-90.

Jiang, Pei-Hong, et al., "Tumor Protein p53-Induced Nuclear Protein 1 (TP53INP1) in Spontaneous Chronic Pancreatitis in the WBN/Kob Rat: Drug Effects on Its Expression in the Pancreas," *J. Pancreas.* (2004) 5(4):205-16.

Jin, Kunlin, et al., "Two caspase-2 transcripts are expressed in rat hippocampus after global cerebral ischemia," *J. Neurochem.* (2002) 81:25-35.

Kajstura, Jan, et al., "Necrotic and apoptotic myocyte cell death in the aging heart of Fischer 344 rats," *Am J Physiol.*, 1996, 271: H1215-1228.

Kannan, Karuppiah, et al., "Profile of gene expression regulated by induced p53: connection to the TGF-L family," *FEBS Lett.* (2000) 470(1): 77-82.

Katunuma, N., et al., "Novel Procaspase-3 Activating Cascade Mediated by Lysoapoptases and its Biological Significances in Apoptosis," *Advan. Enzyme Regul.* (2001) 41:237-250.

Kayo, Tsuyoshi, et al., "Influences of aging and caloric restriction on the transcriptional profile of skeletal muscle from rhesus monkeys," *PNAS*, 2001, 98:5093-5098.

Kerr, LE, et al., "Mice overexpressing human caspase 3 appear phenotypically normal but exhibit increased apoptosis and larger lesion volumes in response to transient focal cerebral ischaemia," *Cell Death Differ.* (2004) 11(10): 1102-11.

Kirkin, Vladimir, et al., "The role of Bcl-2 family members in tumorigenesis," *BBA—Mol. Cell. Res.* (2004) 1644(2-3):229-49.

Kondo, Shinya, et al., "Modulation of apoptosis by endogenous Bcl-xL expression in MKN-45 human gastric cancer cells," et al., *Oncogene* (1998) 17:2585-91.

Krumschnabel, G., et al., "Caspase-2: killer, savior and safeguard—emerging versatile roles for an ill-defined caspase," *Oncogene* (2009) 28(35): 3093-96.

Kyng, Kasper J., et al., "Gene expression profiling in Werner syndrome closely resembles that of normal aging," *PNAS*, 2003, 100:12259-12264.

Lacelle, Chantale, et al., "Identification of high caspase-3 mRNA expression as a unique signature profile for extremely old individuals," *Mech Ageing Dev.*, 2002, 123: 1133-1144.

Lamkanfi, M., et al., "Alice in caspase land. A phylogenetic analysis of caspases from worm to man," *Cell Death Differ.* (2002) 9: 358-361.

Lee, Cheol-Koo, et al., "Gene Expression Profile of Aging and Its Retardation by Caloric Restriction," *Science*, 1999, 285:1390-1393.

Li, Peng, et al., "Mitochondrial Activation of Apoptosis," *Cell* (2004) S116: S57-S59.

Logue, Susan E., et al., "Caspase activation cascades in apoptosis," *Biochem. Soc. Trans.* (2008) 36(1): 1-9.

Martin, Lee J., "Biology of Mitochondria in Neurodegenerative Diseases," Prog. Mol. Biol. Transl. Sci. (2012) 107:355-415.

Martinon, F., et al., "Inflammatory caspases and inflammasomes: master switches of inflammation," *Cell Death Differ.* (2007) 14:10-22.

Mignard, V., et al., "Bioactive lipids and the control of Bax pro-apoptotic Activity," *Cell Death and Disease*, (2014) 5:e1266.

N'Guessan, Prudence, et al., "Absence of Tumor Suppressor Tumor Protein 53-Induced Nuclear Protein 1 (TP53INP1) Sensitizes Mouse Thymocytes and Embryonic Fibroblasts to Redox-Driven Apoptosis," *Antioxid. Redox. Signal.* (2011) 15(6):1639-53.

Nakagawa, Toshiyuki, et al., "Caspase-12 mediates endoplasmic-reticulum-specific apoptosis and cytotoxicity by amyloid-β," *Nature* (2000) 403:98-103.

Narkilahti, Susanna, et al., "Increased Expression of Caspase 2 in Experimental and Human Temporal Lobe Epilepsy," *Neuromolecular Med.* (2007) 9(2): 129-44.

Nicholson, DW., "Caspase structure, proteolytic substrates, and function during apoptotic cell death," *Cell Death Differ.* (1999) 6:1028-42.

Okamura, Shu, et al., "p53DINP1, a p53-Inducible Gene, Regulates p53-Dependent Apoptosis," *Mol. Cell* (2001) 8(1): 85-94.

Olsson, M., et al., "DISC-mediated activation of caspase-2 in DNA damage-induced apoptosis," *Oncogene* (2009) 28(19): 1949-59.

Park, Sang-Kyu, et al., "Gene Expression Profiling of Aging in Multiple Mouse Strains: Identification of Aging Biomarkers and Impact of Dietary Antioxidants," *Aging Cell*, 2009 8:484-495.

Park, Young Chul, et al., "A Novel Mechanism of TRAF Signaling Revealed by Structural and Functional Analyses of the TRADD—TRAF2 Interaction," *Cell* (2000) 101(7):777-87.

Pirouzpanah, Mohammad Bagher, et al., "Silibilin-Induces Apoptosis in Breast Cancer Cells by Modulating p53, p21, Bak and Bcl-xl Pathways," *Asian Pac. J. Cancer Prev.* (2015) 16(5):2087-92.

Porter, Alan G., et al., "Emerging roles of caspase-3 in apoptosis," *Cell Death Differ.* (1999) 6(2):99-104.

Pozueta, Julio, et al., "Caspase-2 is required for dendritic spine and behavioral alterations in J20 APP transgenic mice," *Nat. Commun.* (2013) 4:1939.

Ramírez, Maria José, et al., "Increased apoptosis dependent on caspase-3 activity in polymorphonuclear leukocytes from patients with cirrhosis and ascites," *J. Hepatol.* (2004) 41(1): 44-8.

Saati, Talal Al, et al., "Oxidative Stress Induced by Inactivation of TP53INP1 Cooperates with KrasG12D to Initiate and Promote Pancreatic Carcinogenesis in the Murine Pancreas," *Am. J. Pathol.* (2013) 182(6): 1996-2004.

Sainski, Amy M., et al., "Casp8p41 generated by HIV protease kills CD4 T cells through direct Bak activation," *J. Cell Biol.* (2014) 206(7):867-76.

Saleh, Maya, et al., "Differential modulation of endotoxin responsiveness by human caspase-12 polymorphisms," *Nature* (2004) 429, 75-79.

Saleh, Maya, et al., "Enhanced bacterial clearance and sepsis resistance in caspase-12-deficient mice," *Nature* (2006) 440:1064-68.

Salvesen, Guy S., "Caspases: opening the boxes and interpreting the arrows," *Cell Death Differ.* (2002) 9:3-5.

Sancho, Ana, et al., "DOR/Tp53inp2 and Tp53inp1 Constitute a Metazoan Gene Family Encoding Dual Regulators of Autophagy and Transcription," *PLoS One* (2012) 7(3):e34034.

(56) References Cited

OTHER PUBLICATIONS

Shimizu, Shigeomi, et al., "Essential Role of Voltage-dependent Anion Channel in Various Forms of Apoptosis in Mammalian Cells," *J. Cell Biol.* (2001) 152(2): 237-250.

Southworth, Lucinda K., et al., "Aging Mice Show a Decreasing Correlation of Gene Expression within Genetic Modules," *PLoS Genetics*, 2009, 5:e1000776.

Sugiyama, Tomoyasu, et al., "Activation of mitochondrial voltage-dependent anion channel by a pro-apoptotic BH3-only protein Bim," *Oncogene* (2002) 21(32): 4944-56.

Tinel, Antoine, et al., "The PIDDosome, a Protein Complex Implicated in Activation of Caspase-2 in Response to Genotoxic Stress," *Science* (2004) 304(5672): 843-46.

Tomasini, Richard, et al., "Molecular and Functional Characterization of the Stress-induced Protein (SIP) Gene and Its Two Transcripts Generated by Alternative Splicing," *J. Biol. Chem* (2001) 276(47):44185-92.

Tomasini, Richard, et al., "TP53INP1 is a novel p73 target gene that induces cell cycle arrest and cell death by modulating p73 transcriptional activity," *Oncogene* (2005) 24: 8093-8104.

Tomasini, Richard, et al., "TP53INP1s and Homeodomain-interacting Protein Kinase-2 (HIPK2) are Partners in Regulating p53 Activity," *J. Biol. Chem.* (2003) 278: 37722-29.

Tong, Qiang-Song, et al., "BAK overexpression mediates p53-independent apoptosis inducing effects on human gastric cancer cells," *BMC Cancer* (2004) 4:33.

Tyagi, Alpna, et al., "Silibinin activates p53-caspase 2 pathway and causes caspase-mediated cleavage of Cip1/p21 in apoptosis induction in bladder transitional-cell papilloma RT4 cells: evidence for a regulatoiy loop between p53 and caspase 2," *Carcinogenesis* (2006) 27(11): 2269-80.

Ueda, Norishi, "Ceramide-Induced Apoptosis in Renal Tubular Cells: A Role of Mitochondria and Sphingosine-1-Phoshate," *Int. J. Mol. Sci.* (2015) 16(3): 5076-5124.

Vigneswara, Vasanthy, et al., "Combined suppression of CASP2 and CASP6 protects retinal ganglion cells from apoptosis and promotes axon regeneration through CNTF-mediated JAK/STAT signaling," *Brain* (2014) 137(6): 1656-75.

Walters, Jad, et al., "A constitutively active and uninhibitable caspase-3 zymogen efficiently induces apoptosis," *Biochem. J.* (2009) 424(3): 335-345.

Wang, Ning, et al., "Involvement of PDCD5 in the regulation of apoptosis in fibroblast-like synoviocytes of rheumatoid arthritis," *Apoptosis* (2007) 12:1433-1441.

Westphal, D., et al., "Building blocks of the apoptotic pore: how Bax and Bak are activated and oligomerize during apoptosis," *Cell Death Differ.*, (2014) 21:196-205.

Xu, Lanjun, et al., "PDCD5 interacts with p53 and functions as a positive regulator in the p53 pathway," *Apoptosis* (2012) 17:1235-45.

Xue, Yali, et al., "Spread of an Inactive Form of Caspase-12 in Humans is Due to Recent Positive Selection," *Am. J. Hum. Genet.* (2006) 78(4): 659-670.

Yamamoto, Kei, et al., "Hypoxia-induced renal epithelial cell death through caspase-dependent pathway: Role of Bcl-2, Bcl-xL and Bax in tubular injury," *Int. J. Mol. Med.* (2004) 14(4): 633-40.

Yazidi-Belkoura, Ikram El, et al., "Tumor Necrosis Factor Receptor-associated Death Domain Protein is Involved in the Neurotrophin Receptor-mediated Antiapoptotic Activity of Nerve Growth Factor in Breast Cancer Cells," *J. Biol. Chem.* (2003) 278(19):16952-6.

Zhivotovsky, Boris, et al., "Caspase-2 function in response to DNA damage," *Biochem. Biophys. Res. Commun.* (2005) 331(3): 859-67.

Zhu, Nongliao, et al., "Hepatitis C Virus Core Protein Enhances FADD-Mediated Apoptosis and Suppresses TRADD Signaling of Tumor Necrosis Factor Receptor," *Virology* (2001) 283(2):178-87.

Jagadeesha, D.K., et al., "Tempol Therapy Attenuates Medial Smooth Muscle Cell Apoptosis and Neointima Formation After Balloon Catheter Injury in Carotid Artery of Diabetic Rats," *American Journal of Physiology, Heart and Circulatory Physiology*. (2005) 289(3):H1047-H1053.

Jiang, Youde, et al., "Age-Associated Increase in Cleaved Caspase 3 Despite Phosphorylation of IGF-1 Receptor in the Rat Retina," *The Journals of Gerontology, Series A: Biological Sciences and Medical Sciences*. (2009) 64A(11):1154-1159.

Slater, Andrew F.G., et al., "Nitrone Spin Traps and a Nitroxide Antioxidant Inhibit a Common Pathway of Thymocyte Apoptosis," *The Biochemical Journal*. (1995) 306(3):771-778.

International Search Report and Written Opinion for PCT Application No. PCT/US2017/032743, dated Aug. 17, 2017.

\* cited by examiner

DECREASING EXPRESSION LEVEL OF APOPTOSIS-RELATED GENES BY TREATING A HUMAN SUBJECT WITH A NITROXIDE

BACKGROUND

Field

The present disclosure relates generally to the field of apoptosis biology and more particularly to treating human subjects having an increased level of apoptosis or expression of a gene associated with the apoptosis pathway. The present disclosure further relates to treating human subjects having or at risk of having a disease associated with an increased level of apoptosis or expression of a gene associated with the apoptosis pathway with a nitroxide.

Description of the Related Art

Apoptosis is a process of programmed cell death that occurs in multicellular organisms. Through apoptosis, cells commit suicide as a way to clear unwanted or damaged cells or to prevent uncontrolled growth. Thus, apoptosis plays an essential role in tissue development and function. Dysregulation in the apoptotic pathway, for example, decrease or increase in apoptosis, can lead to a number of diseases and conditions such as cancers, autoimmune diseases, inflammatory diseases, neurodegenerative diseases and bacterial or viral infections.

SUMMARY

The present disclosure provides methods for treating an individual in need thereof. The methods, in some embodiments, include identifying an individual in need of a reduced expression level of a gene associated with the apoptosis pathway; and administering to the individual an effective amount of a nitroxide antioxidant to reduce the level of expression of the gene associated with the apoptosis pathway. In some embodiments, the expression level of the gene associated with the apoptosis pathway is reduced. In some embodiments, the expression level of the gene associated with the apoptosis pathway is reduced in a tissue selected from the group consisting of a skin tissue, an immune tissue, a pancreatic tissue and a neuronal tissue.

Some embodiments disclosed herein provide methods for treating, ameliorating, preventing or inhibiting the progression of a disease associated with an increased level of apoptosis in an individual in need thereof, comprising: identifying an individual affected by or at risk for a disease associated with an increased level of apoptosis; and administering to the individual an effective amount of a nitroxide antioxidant to reduce the level of expression of a gene associated with the apoptosis pathway. In some embodiments, the disease associated with an increased level of apoptosis can be selected from the group consisting of a neurodegenerative disease, an immune system dysfunction, a cardiovascular dysfunction, muscle atrophy, an intestinal disorder, a kidney disease, an autoimmune disease, acquired immune deficiency syndrome (AIDS), and any combination thereof. In some embodiments, the neurodegenerative disease is Alzheimer's disease. In some embodiments, the neurodegenerative disease is Huntington's disease. In some embodiments, the neurodegenerative disease is temporal lobe epilepsy. In some embodiments, the expression level of the gene associated with the apoptosis pathway in a neuronal cell is reduced. In some embodiments, the gene associated with the apoptosis pathway is selected from the group consisting of Bak1, Pdcd5, Casp2, Tradd, Tp53inp1, Casp3 and Casp12. In some embodiments, the nitroxide antioxidant is 4-hydroxy-2,2,6,6-tetramethylpiperidine-1-oxyl. In some embodiments, the effective amount of a nitroxide antioxidant is within a range of 0.01-300 mg/kg. In some embodiments, the effective amount of a nitroxide antioxidant is within a range of 0.1-250 mg/kg. In some embodiments, the effective amount of a nitroxide antioxidant is within a range of 1-200 mg/kg. In some embodiments, the effective amount of a nitroxide antioxidant is within a range of 2-150 mg/kg. In some embodiments, the effective amount of a nitroxide antioxidant is within a range of 5-125 mg/kg. In some embodiments, the effective amount of a nitroxide antioxidant is within a range of 7-100 mg/kg. In some embodiments, the effective amount of a nitroxide antioxidant is within a range of 10-75 mg/kg. In some embodiments, the effective amount of a nitroxide antioxidant is within a range of 15-30 mg/kg.

Some embodiments disclosed herein provide methods for increasing or restoring the level of immune response to a bacterial infection in an individual in need thereof, comprising: identifying an individual having a decreased level of immune response to a bacterial infection; and administering to the individual an effective amount of a nitroxide antioxidant to reduce the level of expression of a gene associated with the apoptosis pathway. In some embodiments, the individual is in need of a reduced expression level of the gene associated with the apoptosis pathway. In some embodiments, the expression level of the gene associated with the apoptosis pathway in a leukocyte is reduced. In some embodiments, the gene associated with the apoptosis pathway is selected from the group consisting of Bak1, Pdcd5, Casp2, Tradd, Tp53inp1, Casp3 and Casp12. In some embodiments, the nitroxide antioxidant is 4-hydroxy-2,2,6,6-tetramethylpiperidine-1-oxyl.

Some embodiments disclosed herein provide methods for treating, ameliorating, preventing or inhibiting the progression of a psychiatric condition in an individual in need thereof, comprising: identifying an individual affected by or at risk for a psychiatric condition; and administering to the individual an effective amount of a nitroxide antioxidant to reduce the level of expression of a gene associated with the apoptosis pathway. In some embodiments, the individual is in need of a reduced expression level of the gene associated with the apoptosis pathway. In some embodiments, the psychiatric condition is selected from the group consisting of schizophrenia, bipolar disease, psychotic symptoms, cognitive impairment and dementia. In some embodiments, the expression level of the gene associated with the apoptosis pathway in a neuronal cell is reduced. In some embodiments, the expression level of the gene associated with the apoptosis pathway in a leukocyte is reduced. In some embodiments, the gene associated with the apoptosis pathway is selected from the group consisting of Bak1, Pdcd5, Casp2, Tradd, Tp53inp1, Casp3 and Casp12. In some embodiments, the nitroxide antioxidant is 4-hydroxy-2,2,6,6-tetramethylpiperidine-1-oxyl.

Some embodiments disclosed herein provide methods for counteracting or preventing stress-induced apoptosis in an individual in need thereof, comprising: identifying an individual affected by or at risk for stress-induced apoptosis; and administering to the individual an effective amount of a nitroxide antioxidant to reduce the level of expression of a gene associated with the apoptosis pathway. In some embodiments, the individual is in need of a reduced expression level of the gene associated with the apoptosis pathway. In some embodiments, the stress can be selected from the group consisting of UV, ethanol, heat shock and oxidative stress. In some embodiments, the stress-induced apoptosis comprises acute pancreatitis. In other embodiments, the expression level of the gene associated with the apoptosis pathway is reduced. In some embodiments, the expression level of the gene associated with the apoptosis pathway is reduced in a tissue selected from the group consisting of a skin tissue, an immune tissue, a pancreatic tissue, and a neuronal tissue. In some embodiments, the gene associated with the apoptosis pathway is selected from the group consisting of Bak1, Pdcd5, Casp2, Tradd, Tp53inp1, Casp3 and Casp12. In some embodiments, the nitroxide antioxidant is 4-hydroxy-2,2,6,6-tetramethylpiperidine-1-oxyl.

Some embodiments disclosed herein provide methods for decreasing the expression level of a gene in an individual in need thereof, comprising: identifying an individual having an increased expression level of a gene associated with the apoptosis pathway; and administering to the individual an effective amount of a nitroxide antioxidant to reduce the level of expression of the gene associated with the apoptosis pathway. In some embodiments, the expression level of the gene associated with the apoptosis pathway is reduced. In some embodiments, the expression level of the gene associated with the apoptosis pathway is reduced in a tissue selected from the group consisting of a skin tissue, an immune tissue, a pancreatic tissue, and a neuronal tissue. In some embodiments, the gene associated with the apoptosis pathway is selected from the group consisting of Bak1, Pdcd5, Casp2, Tradd, Tp53inp1, Casp3 and Casp12. In some embodiments, the increased expression level of the gene is age-related. In some embodiments, the individual is over the age of 35. In some embodiments, the individual is over the age of 45. In some embodiments, the individual is over the age of 55. In some embodiments, the individual is over the age of 65. In some embodiments, the increased expression level of the gene is disease-related. In some embodiments, the disease is selected from the group consisting of a neurodegenerative disease, an immune system dysfunction, a cardiovascular dysfunction, muscle atrophy, an intestinal disorder, a kidney disease, an autoimmune disease, acquired immune deficiency syndrome (AIDS), and any combination thereof. In some embodiments, the neurodegenerative disease is Alzheimer's disease. In some embodiments, the neurodegenerative disease is Huntington's disease. In some embodiments, the neurodegenerative disease is temporal lobe epilepsy. In some embodiments, the disease is age-related. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl.

Some embodiments disclosed herein provide methods for preventing a disease in an individual in need thereof, comprising: identifying an individual at risk of a disease having an increased expression level of a gene associated with the apoptosis pathway; and administering to the individual an effective amount of a nitroxide antioxidant to reduce the level of expression of the gene associated with the apoptosis pathway. In some embodiments, the expression level of the gene associated with the apoptosis pathway is reduced. In some embodiments, the expression level of the gene associated with the apoptosis pathway is reduced in a tissue selected from the group consisting of a skin tissue, an immune tissue, a pancreatic tissue, and a neuronal tissue. In some embodiments, the gene associated with the apoptosis pathway is selected from the group consisting of Bak1, Pdcd5, Casp2, Tradd, Tp53inp1, Casp3 and Casp12. In some embodiments, the increased expression level of the gene is age-related. In some embodiments, the individual is over the age of 35. In some embodiments, the individual is over the age of 45. In some embodiments, the individual is over the age of 55. In some embodiments, the individual is over the age of 65. In some embodiments, the increased expression level of the gene is related to the individual's family history, health conditions, medical history, habits, or a combination thereof. In some embodiments, the disease is selected from the group consisting of a neurodegenerative disease, an immune system dysfunction, a cardiovascular dysfunction, muscle atrophy, an intestinal disorder, a kidney disease, an autoimmune disease, acquired immune deficiency syndrome (AIDS), and any combination thereof. In some embodiments, the neurodegenerative disease is Alzheimer's disease. In some embodiments, the neurodegenerative disease is Huntington's disease. In some embodiments, the neurodegenerative disease is temporal lobe epilepsy. In some embodiments, the disease is age-related. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl.

Some embodiments disclosed herein provide methods for treating in an individual having or at risk of developing a disease due to aging, comprising: identifying an individual over the age of 35 at risk of developing a disease; and administering to the individual an effective amount of a nitroxide antioxidant to reduce the level of expression of a gene associated with the apoptosis pathway. In some embodiments, the individual has an increased expression level of the gene associated with the apoptosis pathway. In some embodiments, the expression level of the gene associated with the apoptosis pathway is reduced. In some embodiments, the expression level of the gene associated with the apoptosis pathway is reduced in a tissue selected from the group consisting of a skin tissue, an immune tissue, a pancreatic tissue, and a neuronal tissue. In some embodiments, the gene associated with the apoptosis pathway is selected from the group consisting of Bak1, Pdcd5, Casp2, Tradd, Tp53inp1, Casp3 and Casp12. In some embodiments, the increased expression level of the gene is age-related. In some embodiments, the individual is over the age of 45. In some embodiments, the individual is over the age of 55. In some embodiments, the individual is over the age of 65. In some embodiments, the increased expression level of the gene is related to the individual's family history, health conditions, medical history, habits, or a combination thereof. In some embodiments, the disease is selected from the group consisting of a neurodegenerative disease, an immune system dysfunction, a cardiovascular dysfunction, muscle atrophy, an intestinal disorder, a kidney disease, an autoimmune disease, acquired immune deficiency syndrome (AIDS), and any combination thereof. In some embodiments, the neurodegenerative disease is Alzheimer's disease. In some embodiments, the neurodegenerative disease is Huntington's disease. In some embodiments, the neurodegenerative disease is temporal lobe epilepsy. In some embodiments, the disease is age-related. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl.

DETAILED DESCRIPTION

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N Y 1989). For purposes of the present disclosure, the following terms are defined below.

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the term "expression" means the detection of a gene product that is expressed or produced by a nucleic acid molecule by standard molecular biology methods, which gene product refers to e.g. an unspliced RNA, an mRNA, a splice variant mRNA, a polypeptide, a post-translationally modified polypeptide, a splice variant polypeptide and specifically products made using an RNA gene product as a template, e.g. cDNA of the RNA.

As used herein, "differential expression" of a gene means that the expression of the gene is at a higher level ("increased expression") or lower level ("decreased expression") in a human subject suffering from a disease such as neurodegenerative disease or bacterial infection relative to its expression in a normal or control subject. Differential expression includes both quantitative and qualitative differences in the temporal or cellular expression pattern in a gene or its expression products among, for example, normal and diseased cells, or among cells which have undergone different disease events or disease stages.

As used herein, "to reduce the level of expression" of a gene means causing the expression of the gene to decrease by treating the human subject with a compound, such as a nitroxide antioxidant, so that the expression level of the gene after treatment is lower than the expression level of the gene before treatment in the human subject.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

Methods for Decreasing the Expression Level of a Gene

Some embodiments disclosed herein provide methods for decreasing the expression level of a gene in an individual in need thereof, comprising identifying an individual having an increased expression level of a gene associated with the apoptosis pathway; and administering to the individual an effective amount of a nitroxide antioxidant to reduce the level of expression of the gene associated with the apoptosis pathway.

The increased expression level of a gene associated with the apoptosis pathway could be related to a number of factors, such as age, disease, family history, health conditions, medical history, habits, or a combination thereof. In some embodiments, the disease is selected from the group consisting of a neurodegenerative disease, an immune system dysfunction, a cardiovascular dysfunction, muscle atrophy, an intestinal disorder, a kidney disease, an autoimmune disease, acquired immune deficiency syndrome (AIDS), and any combination thereof.

Aging

Aging is major biological process and a risk factor for many diseases. Untimely loss of irreplaceable cells in certain tissues is one mechanism by which deregulated apoptosis can exert a detrimental effect during the aging process. Wang et al., Handbook of the Biology of Aging pp. 246-260 ($5^{th}$ ed. 2001), the content of which is hereby incorporated by reference in its entirety. Excessive apoptotic cell death may result in aberrant cell loss and organ atrophy, pathological events that under lie neurodegenerative diseases, immune system dysfunction, cardiovascular dysfunction, muscle atrophy, intestinal disorders, and kidney diseases. One of the classical examples of an age-related phenomenon associated with an undesired diminution in cell number is cardiovascular dysfunction. A common event in the execution of apoptotic cell death is the activation of a family of caspases. Overexpression of caspase 1 or 3 is sufficient to trigger apoptosis.

Gene expression profiling studies in aging mouse strains have identified a number of biomarkers that have altered expression levels due to aging. See Lee et al., Science 1999, 285:1390-1393; Park et al., Aging Cell 2009 8:484-495; Kayo et al., PNAS 2001, 98:5093-5098; Bodyak et al., Nucleic Acids Res. 2002, 30:3788-3794; Glass et al., Genome Biol. 2013, 14:R75, the contents of which are hereby incorporated by reference in their entireties. Southworth et al. have identified a number of functional gene groups that change co-expression with age. PLoS Genetics 2009, 5:e1000776, the content of which is hereby incorporated by reference in its entirety. Age-related alteration in expression level of genes associated with the apoptosis pathway has been widely reported. See Cooper, J. Clin. Exp. Pathol. 2012, S4; Edwards et al., BMC Genomics 2007, 8:80; Pedro de Magalhães et al., Bioinformatics 2009, 25:875-881; Kyng et al., PNAS 2003, 100:12259-12264, the contents of which are hereby incorporated by reference in their entireties.

Neurodegenerative Diseases

An increase in apoptosis, particularly in post-mitotic tissues, may lead to excessive cell loss and a function decline in tissues, as is observed in neurodegenerative diseases. Cooper, supra. Several studies have reported a linked between multiple caspases and Alzheimer's disease, and elevated expression and activation of caspases are found in the brain of Alzheimer's disease patients, such as caspases-1, -2, -3, -5, -6, -7, -8 and -9.

Caspase activity has also been linked to the development of Huntington's disease. As the disease progress, caspase-3 transcription is up-regulated and elevated levels of caspase-3 activity are detected. Moreover, caspase-8 and caspase-9 activation, as well as the release of cytochrome c have also been demonstrated in Huntington's disease.

Aging Immune System

The deterioration of the immune system is believed to contribute to morbidity and mortality in aging humans. Aging is associated with thymic involution, lymphopenia, and a progressive deterioration in T cell function. Cooper, supra. This decline in T cell function is believed to play a role in age-enhanced susceptibility to infection, autoimmunity and cancer. Age-dependent increase in apoptotic activity and caspase activity has been reported in both human and murine T cells and B cells. Lacelle et al., Mech Ageing Dev 2002, 123: 1133-1144. used quantitative RT-PCR to screen the PBMCs from human subjects ranging from 2-102 yrs of age where they observed an increase in caspase-1 and caspase-3 mRNA levels in old (70-89 years) and extremely old (>90 years) humans compared to those in younger age groups, the content of which is hereby incorporated by reference in its entirety. Moreover, CD4+ and CD8+ T cells from older human subjects are reported to display increased expression of TNFR1 and TRADD, and increased caspase-8 and caspase-3 activity upon stimulation with TNF-α.

Cardiovascular Diseases

There is increasing evidence of a relationship between apoptosis and cardiovascular disease, particularly for the heart diseases common to the elderly populations, including ischemic heart disease and congestive heart failure. The aging process in the heart is characterized by a significant loss of cardiac myocytes with the base-line level of apoptosis higher in older compared to younger animals. Kajstura et al., Am J Physiol 1996, 271: H1215-1228, the content of which is hereby incorporated by reference in its entirety. Moreover, increased levels of cardiomyocyte apoptosis are detected following ischemic attacks suggesting that apoptosis in the aging heart is a contributing factor for the elevated MI-related morbidities and mortalities observed in elderly patients. In addition to age-related cell loss, apoptosis has been linked to other age-related vascular diseases, including atherosclerosis.

Human Subject Identification

The present disclosure relates to methods of treating alteration in the level of gene expression and diseases associated with an altered expression level of a gene associated with the apoptosis pathway. More specifically, disclosed herein are methods of treating a human subject having or at risk of a disease associated with an altered apoptosis level and/or expression level of a gene associated with the apoptosis pathway, or a human subject in need of a decrease in gene expression levels, such as those genes associated with the apoptosis pathway, and/or a decrease in apoptosis levels. In some embodiments, the human subject can be identified based on the human subject's gene expression level, apoptosis level, family history, health conditions, medical history, habits, or a combination thereof.

In some embodiments, the human subject is identified as having an increased expression level of a gene, such as a gene associated with the apoptosis pathway. In some embodiments, the increased expression level of the gene can be in comparison to a normal expression level. In some embodiments, the increased expression level of the gene can be at least 10%, at least 20%, at least 30%, at least 40%, at least 50%, at least 60%, at least 70%, at least 80%, at least 90%, at least 100%, at least 200%, at least 300%, at least 400%, at least 500%, in comparison to a normal expression level. A "normal expression level" as used herein can refer to an expression level of the gene observed in a reference cell, tissue, organ or individual. For example, "normal expression level" can refer to the expression level of a gene in an individual that is less than 50, 45, 40, 35, 30, 25, 20, 15 years old, or is a at an age that is between any of the two above mentioned values. In some embodiments, "normal expression level" of a gene can refer to the expression level of the gene in an individual that is free of any disease or is not at risk of developing a disease, or in a group of disease-free individuals. In some embodiments, "normal expression level" of a gene can refer to the expression level of the gene in an unaffected cell, tissue, organ of the individual being treated. In some embodiments, "normal expression level" of a gene can refer to the expression level of a gene in correlation to another gene within a genetic module. A genetic module can refer to a group of genes that are co-regulated or co-express, or share genetic functions using Gene Ontology categories. In some embodiments, the increased expression level of the gene associated with the apoptosis pathway is in comparison to the normal expression level of the gene in a tissue selected from the group consisting of a skin tissue, an immune tissue, a cardiac tissue, a kidney tissue, a pancreatic tissue, and a neuronal tissue.

Regardless of the cause of the increased expression level or upregulation, some common terminology can be used. In some embodiments, the expression level of a gene (such as Bak1, Pdcd5, Casp2, Tradd, Tp53inp1, Casp3 or Casp12) in a human subject is considered to be increased or upregulated if the increase in the expression level of that gene is statistically significant compared to that of a control or a reference. The control or reference can be, for example, a normal healthy population, a population at large, a collection of individuals of the same age or condition or sex, or the same human subject at a different time (e.g., at an earlier time of life when the human subject does not have the disease or condition that results in the increase).

In some embodiments, a normal healthy population or a population at large can be a population having the same or similar gender, age, and/or race, compared to the human subject. In some embodiments, the expression level of the gene in the control or reference can be the mean or median expression level of the gene in control subjects in the control or reference subjects in the reference. The increase in expression level can be statistically significant if the probability of the observed difference occurring not by chance, the confidence level, is greater than a threshold. The threshold can be, or be about, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values.

In some embodiments, the increase in expression level can be, or be about, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. In some embodiments, the increase in expression level can be at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or more.

In some embodiments, the human subject may have an age that is, is about, or is at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 years old.

In some embodiments, the human subject is identified based on the human subject's expression profiles of a gene.

Non-limiting exemplary methods for determining the human subject's expression profiles include: amplification techniques such as PCR and RT-PCR (including quantitative variants), hybridization techniques such as in situ hybridization, microarrays, blots, and others, and high throughput sequencing techniques like Next Generation Sequencing (Illumina, Roche Sequencer, Life Technologies SOLID™), Single Molecule Real Time Sequencing (Pacific Biosciences), True Single Molecule Sequencing (Helicos), or sequencing methods using no light emitting technologies but other physical methods to detect the sequencing reaction or the sequencing product, like Ion Torrent (Life Technologies). Non-limiting exemplary methods for determining the human subject's expression profiles include: binding techniques such as ELISA, immunohistochemistry, microarray and functional techniques such as enzymatic assays.

In some embodiments, the human subject is identified based on the age of the human subject. For example, the human subject can be identified as having an age that is, is about, is at least, is greater than, 20, 25, 30, 35, 40, 45, 50, 55, 60, 65, 70, 75, 80, 85, 90, 95, 100, or a range between two of any above mentioned values. In some embodiments, the human subject is identified as being at risk of developing a disease, but showing no symptoms of the disease, such as a neurodegenerative disease, an immune system dysfunction, a cardiovascular dysfunction, muscle atrophy, an intestinal disorder, a kidney disease, an autoimmune disease, acquired immune deficiency syndrome (AIDS), and any combination thereof. In some embodiments, the human subject is identified as having or at risk of having an increased level of apoptosis in a tissue, such as a skin tissue, an immune tissue, a cardiac tissue, a kidney tissue, a pancreatic tissue, a neuronal tissue, etc., or a combination thereof. In some embodiments, the increased level of apoptosis can be in comparison to a normal level of apoptosis. In some embodiments, the increased level of apoptosis can be at least 10%, at least 20%, at least 30%, at least 40%, at least 50%, at least 60%, at least 70%, at least 80%, at least 90%, at least 100%, at least 200%, at least 300%, at least 400%, at least 500%, in comparison to a normal level of apoptosis. A "normal level of apoptosis" as used herein can refer to the level of apoptosis observed in a reference cell, tissue, organ or individual. For example, "normal level of apoptosis" can refer to the level of apoptosis in an individual that is less than 50, 45, 40, 35, 30, 25, 20, 15 years old, or is a at an age that is between any of the two above mentioned values. In some embodiments, "normal level of apoptosis" of a gene can refer to the level of apoptosis in an individual that is free of any disease or is not at risk of developing a disease, or in a group of disease-free individuals. In some embodiments, "normal level of apoptosis" of a gene can refer to the level of apoptosis in an unaffected cell, tissue, organ of the individual being treated.

Genes Associated with the Apoptosis Pathway

In some embodiments, the expression level of the gene associated with the apoptosis pathway is reduced using the methods and compositions disclosed herein. In some embodiments, the expression level of the gene can be reduced to a normal expression level, or a level that is lower than a normal expression level. In some embodiments, the expression level of the gene associated with the apoptosis pathway is reduced in a tissue selected from the group consisting of a skin tissue, an immune tissue, a cardiac tissue, a kidney tissue, a pancreatic tissue, and a neuronal tissue.

A "normal expression level" as used herein can refer to an expression level of the gene observed in a reference cell, tissue, organ or individual. For example, "normal expression level" can refer to the expression level of a gene in an individual that is less than 50, 45, 40, 35, 30, 25, 20, 15 years old, or is a at an age that is between any of the two above mentioned values. In some embodiments, "normal expression level" of a gene can refer to the expression level of the gene in an individual that is free of any disease or is not at risk of developing a disease, or in a group of disease-free individuals. In some embodiments, "normal expression level" of a gene can refer to the expression level of the gene in an unaffected cell, tissue, organ of the individual being treated. In some embodiments, "normal expression level" of a gene can refer to the expression level of a gene in correlation to another gene within a genetic module. A genetic module can refer to a group of genes that are co-regulated or co-express, or share genetic functions using Gene Ontology categories.

In some embodiments, administering to the human subject an effective amount of the nitroxide antioxidant results in a reduced expression level of a gene, for example a gene associated with the apoptosis pathway. The gene associated with the apoptosis pathway can be Bak1, Pdcd5, Casp2, Tradd, Tp53inp1, Casp3, or Casp12. The treatment of the human subject with the effective amount of the nitroxide antioxidant can result in a reduced expression level of the gene. For example, the treatment can reduce the expression levels of Bak1, Pdcd5, Casp2, Tradd, Tp53inp1, Casp3, Casp12, or any combination thereof. The reduced expression of the gene counteracts the increase in the expression level of the gene.

In some embodiments, administering to the human subject the effective amount of the nitroxide antioxidant results in a reduced expression level of a gene, for example a gene associated with the apoptosis pathway. Therefore, some embodiments disclosed herein provide methods for treating an individual in need thereof, comprising identifying an individual in need of a reduced expression level of a gene associated with the apoptosis pathway; and administering to the individual an effective amount of a nitroxide antioxidant to reduce the level of expression of the gene associated with the apoptosis pathway. Some embodiments disclosed herein provide treating, ameliorating, preventing or inhibiting the progression of a disease associated with an increased level of apoptosis in an individual in need thereof, comprising identifying an individual affected by or at risk for a disease associated with an increased expression level of a gene associated with the apoptosis pathway; and administering to the individual an effective amount of a nitroxide antioxidant to reduce the level of expression of the gene associated with the apoptosis pathway.

Non-limiting exemplary genes involved in the apoptosis pathway include those involved in the extrinsic apoptosis pathway (FAS, FASLG, TNFRSF10A, TNFRSF10B, TNFRSF10C, TNFRSF10D, TNFRSF11B, TNFSF10, TNFRSF1A, TNF, FADD, CFLAR), those in the Caspases family (CASP1, CASP2, CASP3, CASP4, CASP5, CASP6, CASP7, CASP8, CASP9, CASP10, CASP14), those in the IAPs family (NAIP, BIRC2, BIRC3, XIAP, BIRC5, BIRC6, BIRC7), those involved in the mitochondrial/intrinsic apoptosis pathway (Bcl-2 family: BCL2, MCL1, BCL2L1, BCL2L2, BCL2A1, BCL2L10, BAX, BAK1, BOK, BID, BCL2L11, BMF, BAD, BIK, HRK, PMAIP1, BNIP3, BNIP3L, BCL2L14, BBC3, BCL2L12, and BCL2L13; and other proteins: APAF1, CYCS, DIABLO, HTRA2, AIFM1, and ENDOG).

In some embodiments, the gene associated with the apoptosis pathway can be Bak1, Pdcd5, Casp2, Tradd, Tp53inp1, Casp3 and Casp12. For example, the treatment can result in reduced expression levels of Bak1, Pdcd5, Casp2, Tradd, Tp53inp1, Casp3, Casp12, or any combination thereof. The reduced expression levels of Bak1, Pdcd5, Casp2, Tradd, Tp53inp1, Casp3, Casp12, or any combination thereof, can decrease the level of apoptosis. The decreased level of apoptosis can result in a decrease in or disappearance of signs and symptoms of a disease associated with increased apoptosis, including the curing of the disease associated with increased apoptosis. In some embodiments, the increased expression levels of Bak1, Pdcd5, Casp2, Tradd, Tp53inp1, Casp3, Casp12, or any combination thereof, can increase the level of apoptosis. The increased level of apoptosis can result in a decrease in or disappearance of signs and symptoms of the disease associated with reduced apoptosis, including the curing of the disease associated with reduced apoptosis.

Bak1

Bak1 is also known as BCL2 antagonist/killer 1, Apoptosis Regulator BAK, CDN1, BCL2L7 (Bcl-2-Like Protein 7) or BAK-LIKE. The protein encoded by the Bak1 gene belongs to the BCL2 protein family, which forms oligomers or heterodimers and act as anti- or pro-apoptotic regulators that are involved in a wide variety of cellular activities (Kirkin et al., BBA-Mol. Cell. Res. (2004) 1644(2-3):229-49, the content of which is incorporated by reference in its entirety). In the presence of an appropriate stimulus, Bak1 has been shown to accelerate programmed cell death by binding to and antagonizing the anti-apoptotic action of BCL2 or its adenovirus homolog E1B 19k protein. Bak1 has been shown to be involved in inhibition of the proliferation of MCF-7 breast cancer cells and induction of apoptosis of the MCF-7 cells when the gene was downregulated by a flavonoid compound silibinin (Pirouzpanah et al., Asian Pac. J. Cancer Prev. (2015) 16(5):2087-92, the content of which is incorporated by reference in its entirety).

Bak1 protein localizes to mitochondria, specifically mitochondrial outer membrane (MOM) (Martin, Prog. Mol. Biol. Transl. Sci. (2012) 107:355-415, the content of which is incorporated by reference in its entirety). Bak1 protein has been shown to stimulate mitochondria-mediated apoptosis in two different mechanisms. First, Bak1 protein interacts with and accelerates the opening of the mitochondrial voltage-dependent anion channel, which leads to a loss in membrane potential and the release of cytochrome c from mitochondria (Sugiyama et al., Oncogene (2002) 21(32): 4944-56; Shimizu et al., J. Cell Biol. (2001) 152(2): 237-250; the contents of which are incorporated by reference in their entirety). Loss of cytochrome c from mitochondria disables energy production, and cytosolic cytochrome c instigates a proteolytic cascade that dismantles the cell (Westphal et al., Cell Death Differ. (2014) 21:196-205, the content of which is incorporated by reference in its entirety). Alternatively, Bak1 protein itself forms an oligomeric pore, called mitochondrial apoptosis-induced channel (MAC), in the mitochondrial outer membrane through which pro-apoptotic factors leak in a process called MOM permeabilization (MOMP) (Ueda, Int. J. Mol. Sci. (2015) 16(3): 5076-5124; Mignard et al., Cell Death and Disease (2014) 5:e1266, the contents of which are incorporated by reference in their entireties).

The pro-apoptotic function of Bak1 is shown to contribute to neurodegenerative and autoimmune diseases when overexpressed and cancers when inhibited (Cartron et al., Cell. Signal. (2014) 26(9):1928-34, the content of which is incorporated by reference in its entirety). Dysregulation of Bak1 has been implicated in human gastrointestinal cancers, indicating that the gene plays a part in the pathogenesis of some cancers (Tong et al., BMC Cancer (2004) 4:33, the content of which is incorporated by reference in its entirety; Duckworth and Pritchard, Gastroenterol. (2009) 136(3):943-52, the contents of which are incorporated by reference in their entirety). Also, overexpression of Bak1 has been shown to induce sensitization to apoptosis in MKN-45 gastric cancer cells (Kondo et al. Oncogene (1998) 17:2585-91, the content of which is incorporated by reference in its entirety). Bak1 protein has been shown to interact with the tumor suppressor P53 after exposure to cell stress, and Bak1 gene has been shown to be upregulated by induced p53 expression (Berindan-Neagoe et al., J. Nanosci. Nanotech. (2012) 12:2113-19; Kannan et al., FEBS Lett. (2000) 470(1): 77-82, the contents of which are incorporated by reference in their entireties).

Bak1 has been shown to be involved in the HIV replication pathway, as HIV virus induces apoptosis in T cells via a caspase fragment called Casp8p41, which activates Bak1 to carry out membrane permeabilization, leading to cell death (Sainski et al., J. Cell Biol. (2014) 206(7):867-76, the content of which is incorporated by reference in its entirety). Several alterations in the Bak1 gene were found among patients with ataxia telangiectasia (AT, an autosomal recessive multisystem order characterized by variable immunodeficiency, progressive neurodegeneration, and an increased susceptibility to malignancies), which implies a role of the mitochondrial pathway mediated apoptosis in accelerating and developing of cancers and in immunopathogenesis of AT (Isaian et al., J. of Clin. Immunol. (2010) 30(1):132-7, the content of which is incorporated by reference in its entirety). Thus, decreasing the expression level of Bak1 can be used to treat, ameliorate, prevent or inhibit the progression of a disease associated with an increased level of apoptosis in a human subject with the disease, a human subject having an increased expression of Bak1, or any combination thereof.

Pdcd5

Pdcd5 gene is also known as programmed cell death 5. Pdcd5 encodes an apoptosis-promoting protein that is upregulated during apoptosis where it translocates rapidly from the cytoplasm to the nucleus (Xu et al., Apoptosis (2012) 17:1235-45, the content of which is incorporated by reference in its entirety). Pdcd5 protein has been shown to interact with p53 and function as a positive regulator in the p53 pathway in response to stress signals to regulate transcription and cell cycle arrest (supra).

Overexpression of Pdcd5 was shown to result in enhanced apoptosis and activation of caspase-3 in triptolide-treated (antirheumatic drug-treated) fibroblast-like synoviocytes (FLS) of rheumatoid arthritis (Wang et al., Apoptosis (2007) 12:1433-1441, the content of which is incorporated by reference in its entirety). Inhibition of Pdcd5 gene was shown to have potentially protective effect against cerebral ischemia/reperfusion injury (Chen et al., CNS Neurosci. Ther. (2013) 19(8): 566-576, the content of which is incorporated by reference in its entirety). Also, enhanced expression and nuclear accumulation of Pdcd5 in osteoarthritis chondrocytes were found, indicating the involvement of Pdcd5 in the pathogenesis of osteoarthritis (Cheng et al., Acta. Pharmacol. Sin. (2004) 25(5): 685-90, the content of which is incorporated by reference in its entirety). Thus, decreasing the expression level of Pdcd5 can be used to treat a human subject with rheumatoid arthritis, osteoarthritis, cerebral ischemic stroke, or any combination thereof.

Casp2

Caspases (or cysteine-aspartic acid protease) are cysteine proteases that cleave C-terminal aspartic acid residues on their substrate molecules (Nicholson, Cell Death Differ. (1999) 6:1028-42, the content of which is incorporated by reference in its entirety). Caspases mediate essential key proteolytic events in inflammatory cascades and the apoptotic cell death pathway (Saleh et al., Nature (2004) 429, 75-79, the content of which is incorporated by reference in its entirety). Human caspases functionally segregate into two distinct subfamilies: those involved in cytokine maturation (caspase-1, -4 and -5) and those involved in cellular apoptosis (caspase-2, -3, -6, -7, -8, -9 and -10) (Nicholson, Cell Death Differ. (2002) 9: 358-361, the content of which is incorporated by reference in its entirety).

Caspase 2 is involved in the activation cascade of caspases responsible for apoptosis execution (Logue and Martin, Biochem. Soc. Trans. (2008) 36(1): 1-9, the content of which is incorporated by reference in its entirety). Caspase 2 has been shown to play an important role in cell death induced by genotoxic stress, but unlike other caspases, caspase 2 acts either upstream or downstream in the activation cascade (Zhivotovsky and Orrenius, Biochem. Biophys. Res. Commun. (2005) 331(3): 859-67, the content of which is incorporated by reference in its entirety). It was shown that DNA damage-induced activation of Fas receptor at the cell membrane recruits FADD (Fas-associated protein with death domain), caspase-8, and caspase-2, which cleave and activate the BH3-only protein, Bid, to induce mitochondrial outer membrane permeabilization (MOMP) and mitochondria-mediated apoptosis (Olsson et al., Oncogene (2009) 28(19): 1949-59, the content of which is incorporated by reference in its entirety).

In addition to apoptosis, caspase 2 is shown to have other functions, including roles in DNA repair and tumor suppression (Krumschnabel et al., Oncogene (2009) 28(35): 3093-96, the content of which is incorporated by reference in its entirety). Emerging evidence suggests that caspase 2 may have important functions in stress-induced cell death pathways, cell cycle maintenance, and the suppression of tumorigenesis (Bouchier-Hayes, J. Cell Mol. Med. (2010) 14(6a):1212-24, the content of which is incorporated by reference in its entirety).

Caspase 2 has been shown to associate with a number of proteins involved in apoptosis via CARD (Caspase activation and recruitment domain) domain. Proteins that interact with caspase 2 include a death adaptor molecule RAIDD/CRADD (receptor-interacting protein (RIP)-associated ICH-1/CED-3 homologous protein with a death domain; CASP2 and RIPK1 domain containing adaptor with death domain), apoptosis repressor with caspase recruitment domain (ARC), and death effector filament-forming Ced-4-like apoptosis protein (DEFCAP) (Duan et al., Nature (1997) 385:86-89; Ahmad et al., Cancer Res. (1997) 57:615-19; Zhivotovsky and Orrenius, Biochem. Biophys. Res. Commun. (2005) 331(3): 859-67, the contents of which are incorporated by reference in their entireties). Moreover, caspase 2 has been shown to interact with PIDD (p53-induced protein with a death domain) and RAIDD to form a protein complex called PIDDosome, which may serve as an activation platform for caspase 2 (Tinel and Tschopp, Science (2004) 304(5672): 843-46, the content of which is incorporated by reference in its entirety).

Increased expression of Casp2 gene has been shown to play a role in neurodegenerative disorders including Alzheimer's disease, Huntington's disease, and temporal lobe epilepsy. Caspase-2 is required for the cognitive decline seen in human amyloid precursor protein transgenic mice, implicating caspase-2 as a key driver of synaptic dysfunction in Alzheimer's disease (Pozueta et al., Nat. Commun. (2013) 4: 1939, the content of which is incorporated by reference in its entirety). Caspase 2 has been also shown to be involved in selective neuronal cell death associated with Huntington's diseases in the striatum and cortex (Hermel et al., Cell Death Differ. (2004) 11(4): 424-38, the content of which is incorporated by reference in its entirety). It is shown that caspase-2-mediated programmed cell death participates in the seizure-induced degenerative process in experimental and human temporal lobe epilepsy (Narkilahti et al., Neuromolecular Med. (2007) 9(2): 129-44, the content of which is incorporated by reference in its entirety). Thus, decreasing the expression level of Casp2 can be used to treat a human subject with Alzheimer's disease, Huntington's disease, temporal lobe epilepsy, or any combination thereof.

Activation of Casp2 by silibinin is shown to initiate apoptosis in human bladder transitional-cell papilloma (Tyagi et al., Carcinogenesis (2006) 27(11): 2269-80, the content of which is incorporated by reference in its entirety). Also, it is shown that combined suppression of Casp2 and Casp6 protects retinal ganglion cells from apoptosis and promotes axon regeneration (Vigneswara et al., Brain (2014) 137(6): 1656-75, the content of which is incorporated by reference in its entirety). Caspase-2 induction and activation are shown to be important mediators of neuronal death following transient global cerebral ischemia (Jin et al., J. Neurochem. (2002) 81:25-35, the content of which is incorporated by reference in its entirety). Thus, decreasing the expression level of Casp2 can be used to treat, ameliorate, prevent or inhibit the progression of a disease associated with an increased level of apoptosis in a human subject with the disease, a human subject having an increased expression of Casp2, or any combination thereof.

Tradd

Tumor necrosis factor receptor type 1 (TNFRSF1A)-associated via death domain (TRADD) gene encodes for a death domain containing adaptor molecule that interacts with TNFRSF1A/TNFR1 and mediates programmed cell death signaling and NF-kappa B activation, both of which are major tumor necrosis factor (TNF)-induced responses. TRADD has been shown to interact with the death domain of TNF receptor-1 (TNFR1) to trigger distinct signaling pathways leading to apoptosis and NF-kappa B activation (Hsu et al., Immunity (1996) 4(4): 387-96, the content of which is incorporated by reference in its entirety). In addition, TRADD has been shown to interact strongly with receptor-interacting protein (RIP), another death domain protein that was shown previously to associate with Fas antigen, or an antigen to Fas receptor that leads to programmed cell death (Hsu et al., Immunity (1996) 4(4): 387-96, the content of which is incorporated by reference in its entirety).

TRADD protein binds adaptor protein TRAF2 or TNF receptor associated factor 2, reduces the recruitment of inhibitor-of-apoptosis proteins (IAPs) by TRAF2, and thus suppresses TRAF2 mediated apoptosis. TRAF proteins have been shown to be recruited to activated TNF receptors (TNFRs) either directly or indirectly via the adaptor protein TRADD to regulate apoptosis (Park et al., Cell (2000) 101(7):777-87; Duckett and Thompson, Genes Dev. (1997) 11(21): 2810-21, the contents of which are incorporated by reference in their entirety).

TRADD protein can also interact with receptor TNFRSF6/FAS and adaptor protein Fas-associating protein with death domain (FADD)/MORT1 and is involved in the Fas-induced cell death pathway (Boldin et al., Cell (1996) 85(6): 803-15, the content of which is incorporated by reference in its entirety). The death domain of TRADD has been shown to contain the nuclear import sequence, and expression of the core death domain (nuclear TRADD) results in exclusive nuclear localization and activation of a distinct apoptotic pathway (Bender et al., Cell Death Differ. (2005) 12(5):473-81, the content of which is incorporated by reference in its entirety). In contrast, cytoplasmic TRADD has been shown to activate apoptosis through FADD and caspase-8 activation that is blocked by caspase inhibitors or dominant-negative FADD (Bender et al., Cell Death Differ. (2005) 12(5):473-81, the content of which is incorporated by reference in its entirety). Hepatitis C virus (HCV) core protein has been shown to enhance FADD-mediated apoptosis and suppresses TRADD signaling of tumor necrosis factor receptor 1 or TNFR1 (Zhu et al., Virology (2001) 283(2):178-87, the content of which is incorporated by reference in its entirety).

TRADD has been shown to interact with p75(NTR), a common neutrophin receptor known to initiate intracellular signaling that leads either to cell survival or to apoptosis, in MCF-7 breast cancer cells stimulated by nerve growth factor (NGF) (Yazidi-Belkoura et al., J. Biol. Chem. (2003) 278 (19):16952-6, the content of which is incorporated by reference in its entirety). Also, TRADD has been shown to play a critical role in TRIF-dependent inflammatory responses as well as TNFR1 signaling (Ermolaeva et al., Nature Immunol. (2008) 9:1037-46, the content of which is incorporated by reference in its entirety). Thus, decreasing the expression level of TRADD can be used to treat, ameliorate, prevent or inhibit the progression of a disease associated with an increased level of apoptosis in a human subject, a human subject having an increased expression of TRADD, or any combination thereof.

Tp53inp1

Tp53inp1 is also known as tumor protein p53-inducible nuclear protein 1, Tp53inp1 or stress inducible protein (SIP). Tp53inp1 is an anti-proliferative and pro-apoptotic protein involved in cell stress response which acts as a dual regulator of transcription and autophagy (Sancho et al., PLoS One (2012) 7(3):e34034; Okamura et al., Mol. Cell (2001) 8(1): 85-94, the contents of which are incorporated by reference in their entireties). Tp53inp1 has been shown to promote p53/TP53 phosphorylation on Ser-46 and subsequent apoptosis in response to double-strand DNA breaks (DSB) (Fastje et al., Chem. Biol. Interact. (2012) 196(3): 89-95, the contents of which are incorporated by reference in their entirety). Overexpression of Tp53inp1 was known to induce p53-mediated apoptosis, and Tp53inp1 has been shown to interact with HIPK2 to regulate p53 transcriptional activity (Tomasini et al., J. Biol. Chem. (2003) 278: 37722-29, the content of which is incorporated by reference in its entirety). Tp53inp1 was shown to be both a target gene of the tumor suppressor p53 and an activator of the transcriptional activity of p53, therefore being implicated in a positive feedback loop with p53 (Okamura et al., Mol. Cell (2001) 8(1): 85-94, the content of which is incorporated by reference in its entirety). Tp53inp1 is also known to interact with p'73, a p53 homologue, to positively regulate cell cycle progression and apoptosis, independently from p53 (Tomasini et al., Oncogene (2005) 24: 8093-8104, the content of which is incorporated by reference in its entirety).

Tp53inp1 is referred to as stress inducible protein (SIP) or stress response protein and has been shown to be a major actor in p53/TP53-driven stress response that possesses both a p53-independent intracellular reactive oxygen species (ROS) regulatory function and a p53-dependent transcription regulatory function (Cano et al., Cancer Res. (2009) 69:219-26, the content of which is incorporated by reference in its entirety). In vivo, Tp53inp1 was shown to be induced in pancreatic acinar cells in a mouse model of acute pancreatitis (Tomasini et al., J. Biol. Chem (2001) 276(47): 44185-92, the content of which is incorporated by reference in its entirety). Furthermore, Tp53inp1 expression is shown to be induced in a mouse model of chronic pancreatitis (Jiang et al., J. Pancreas. (2004) 5(4):205-16, the content of which is incorporated by reference in its entirety). Tp53inp1 expression was highly increased in the thymus of mice by thymocyte oxidative stress agent such as γ-irradiation and dexamethosome (N'Guessan et al., Antioxid. Redox. Signal. (2011) 15(6):1639-53, the content of which is incorporated by reference in its entirety).

In vitro, Tp53inp1 was shown to be induced by cell stress agents such as adriamycin, UV irradiation, γ-irradiation, heat shock, methylmethane sulfonate, ethanol, cisplatin, and oxidants such as $H_2O_2$ (Tomasini et al., J. Biol. Chem (2001) 276(47):44185-92; Okamura et al., Mol. Cell (2001) 8(1): 85-94; Tomasini et al., Oncogene (2005) 24: 8093-8104, supra). Tp53inp1 was also shown to be induced by oncogenic stress such as mutated $Ras^{V12}$ and viral E1A protein (Tomasini et al., J. Biol. Chem (2003) 278:37722-29, supra).

Inactivation of Tp53inp1 in mice was shown to increase the level of reactive oxygen species (ROS) and decrease the antioxidant defenses of the Tp53inp1 knockout mice, thus showing a chronic oxidative stress in correlation with an increased susceptibility to develop colitis and colitis-associated cancer (N'Guessan et al., Antioxid. Redox. Signal. (2011) 15(6):1639-53; Cano et al., Cancer Res. (2009) 69:219; Gommeaux et al., Mol. Cell. Biol. (2007) 27(6): 2215-2228, the contents of which are incorporated by reference in their entirety). Tp53inp1 expression was shown to be lost during early pancreatic cancer progression, and it was shown that oxidative stress induced by inactivation of Tp53inp1 cooperates with KrasG12D mutation to initiate and promote pancreatic carcinogenesis in the mouse pancreas (Gironella et al., Proc. Nat'l Acad. Sci. (2007) 104 (41):16170-5; Saati et al., Am. J. Pathol. (2013) 182(6): 1996-2004, the contents of which are incorporated by reference in their entirety). Thus, decreasing the expression level of Tp53inp1 can be used to treat, ameliorate, prevent or inhibit the progression of a disease associated with an increased level of apoptosis in a human subject with the disease, a human subject having an increased expression of Tp53inp1, or any combination thereof.

Casp3

Caspase 3 is one of the effector caspases that orchestrate the direct dismantling of cellular structures, disruption of cellular metabolism, inactivation of cell-death inhibitory proteins and the activation of additional destructive enzymes (Logue and Martin, Biochem. Soc. Trans. (2008) 36(1): 1-9, the content of which is incorporated by reference in its entirety). Activated caspase-3 propagates the caspase signaling cascade by cleaving and activating caspase-2 and caspase-6 downstream and participates in a positive-feedback amplification loop to promote further processing of caspase 9 (Logue and Martin, Biochem. Soc. Trans. (2008) 36(1): 1-9; Cullen and Martin, Cell Death Differ (2009) 16:935-38, the contents of which are incorporated by reference in their entireties).

Caspase 3 exists in a cell as a zymogen (procaspase), which is inactive until a biochemical change causes its activation. The caspase-3 zymogen has virtually no activity until it is cleaved by an initiator caspase during apoptosis (Walters et al., Biochem. J. (2009) 424(3): 335-345, the content of which is incorporated by reference in its entirety).

Caspase-3 is activated in an apoptotic cell by extrinsic (death ligand) and intrinsic (mitochondrial) pathways. The extrinsic apoptosis pathway is triggered through the extracellular ligation of death receptors (e.g., Fas) by their cognate ligands, resulting in receptor clustering, adapter recruitment (e.g., FADD/MORT1), activation of the apical protease caspase 8 (e.g., Fas, FADD, and caspase 8 together form death-inducing signaling complex or DISC), and activation of caspase 3 by caspase 8 (Salvesen, Cell Death Differ (2002) 9:3-5, the content of which is incorporated by reference in its entirety). One example of signaling events that trigger the apoptosis pathway is the introduction of granzyme B, a molecule produced by cytotoxic T lymphocytes and natural killer cells, into cells targeted for apoptosis (Katunuma et al., Advan. Enzyme Regul. (2001) 41:237-250, the content of which is incorporated by reference in its entirety).

The intrinsic pathway responds primarily to cellular stress (e.g., ionizing radiation and cytotoxic drugs) as well as some neurodevelopmental cues, with mitochondria acting as an important integrator (Salvesen, Cell Death Differ (2002) 9:3-5, the content of which is incorporated by reference in its entirety). In intrinsic activation, cytochrome c from mitochondria interacts with caspase-9, apoptosis-activating factor 1 (Apaf-1) and ATP to process and activate procaspase-3 into caspase-3 (Porter and Janicke, Cell Death Differ. (1999) 6(2):99-104; Li et al., Cell (2004) 5116: S57-S59, the contents of which are incorporated by reference in their entireties).

Caspase-3 has been shown to play an indispensable role in apoptotic chromatic condensation and DNA fragmentation (Porter and Janicke, Cell Death Differ. (1999) 6(2):99-104, the content of which is incorporated by reference in its entirety). In addition, caspase 3 has been found to be essential for normal brain development as well as its role in apoptosis (Porter and Janicke, supra). Caspase-3 has been shown to be the predominant caspase involved in the cleavage of amyloid-β precursor protein (APP), which is associated with neuronal death in Alzheimer's disease (Gervais et al., Cell (1999) 97(3):395-406, the content of which is incorporated by reference in its entirety). Thus, decreasing the expression level of Casp3 can be used to treat a human subject with or at risk of developing Alzheimer's disease.

Caspases have been implicated in HIV-mediated apoptosis, and patients with progressive HIV disease demonstrated increased caspase-3 activity (Cicala et al., Proc. Nat'l Acad. Sci. (2000) 97(3):1178-83, the content of which is incorporated by reference in its entirety). It has been also shown that in primary T lymphocytes, HIV-1 envelope proteins induce the activation of caspase-3 and thus promote programmed cell death (Cicala et al., Proc. Nat'l Acad. Sci. (2000) 97(3):1178-83, the content of which is incorporated by reference in its entirety). Thus, decreasing the expression level of Casp3 can be used to treat a human subject with or at risk of an HIV infection.

It is shown that human retinal pigment epithelial (HRPE) cell apoptosis induced by activated monocytes is mediated by caspase-3 activation, indicating potential protection of HRPE cells from monocyte damages in various retinal diseases by downregulating Casp3 (Eliner et al., Trans. Am. Ophthalmol. Soc. (2003) 101:77-91, the content of which is incorporated by reference in its entirety). It was also shown that hypoxia caused renal epithelial cell death induced by caspase-3-like activity-dependent apoptosis, indicating potential reduction or prevention of hypoxic injury in acute renal failure by downregulating Casp3 (Yamamoto et al., Int. J. Mol. Med. (2004) 14(4): 633-40, the content of which is incorporated by reference in its entirety). Mice with overexpressed human caspase 3 exhibited increased apoptosis and larger lesion volumes in response to transient focal cerebral ischemia, implying potential reduction or prevention of hypoxic injury in cerebral ischemic stroke via downregulation of Casp3 (Kerr et al., Cell Death Differ. (2004) 11(10): 1102-11, the content of which is incorporated by reference in its entirety). Polymorphonuclear leukocytes from cirrhotic patients with ascites are shown to have increased apoptosis dependent on caspase-3 activity, implying potential amelioration or prevention of neutropenia in decompensated cirrhosis by downregulating Casp3 (Ramirez et al., J. Hepatol. (2004) 41(1): 44-8, the content of which is incorporated by reference in its entirety).

In addition, it has been shown that elevated serum levels of a cleaved p17 fragment of caspase-3 is a sign of a recent myocardial infarction (Agosto et al., J. Am. Coll. Cardiol. (2011) 57(2): 220-221, the content of which is incorporated by reference in its entirety). Caspase-3 was shown to promote embryonic and hematopoietic stem cell differentiation (Abdul-Ghani and Megeney, Cell Stem Cell (2008) 2(6): 515-16, the content of which is incorporated by reference in its entirety). In another study, expression of caspase-3 in advanced gastric cancer has been shown to be a predictor of poor response to treatment and survival (Amptoulach et al., Med Oncol. (2015) 32(1):416, the content of which is incorporated by reference in its entirety). Age-related differential expression of apoptosis-related genes including Casp3 has been shown in conjunctival epithelial cells, indicating the association between age and apoptosis (Giebel et al., Acta Ophthalmol. Sand. (2005) 83: 471-76, the content of which is incorporated by reference in its entirety). Thus, decreasing the expression level of Casp3 can be used to treat, ameliorate, prevent or inhibit the progression of a disease associated with an increased level of apoptosis in a human subject with or at risk of developing the disease, a human subject having an increased expression of Casp3, or any combination thereof.

Casp12

Casp12 gene is highly related to caspase-1 and other members of the caspase family, known as inflammatory caspases, that process and activate inflammatory cytokines such as interleukin 1 and interleukin 18 (Martinon and Tschopp, Cell Death Differ. (2007) 14:10-22, the content of which is incorporated by reference in its entirety). However, in mice, caspase 12 has been proposed as a mediator of apoptosis induced by endoplasmic reticulum stress including amyloid-β cytotoxicity, suggesting that it might contribute to the pathogenesis of Alzheimer's disease (Nakagawa et al., Nature (2000) 403:98-103, the content of which is incorporated by reference in its entirety).

In humans, Casp12 gene contains a polymorphism for the presence or absence of a premature stop codon. It was shown that the majority of human individuals have the premature stop codon and produce a truncated non-functional protein (Xue et al., Am. J. Hum. Genet. (2006) 78(4): 659-670, the content of which is incorporated by reference in its entirety). The functional form of caspase 12 protein has been shown to be confined to people of African descent and is linked with susceptibility of sepsis and decreased responses to bacterial molecules such as lipopolysaccharide (LPS) (Saleh et al., Nature (2004) 429:75-79, the content of which is incorporated by reference in its entirety). In animal studies, deletion of caspase-12 was shown to render mice resistant to bacterial infection and septic shock (Saleh et al., Nature (2006) 440:1064-68, the content of which is incorporated by reference in its entirety). Hearts obtained from rats given a single dose of doxorubicin were found to have elevated levels of both Casp3 and Casp12, indicating that downregulating Casp12 might be effective in reducing the frequency and/or severity of cardiotoxic sequelae in cancer patients given doxorubicin (Jang et al., FEBS Lett. (2004) 577(3): 483-90, the content of which is incorporated by reference in its entirety). Thus, decreasing the expression level of Casp12 can be used to treat, ameliorate, prevent or inhibit the progression of a disease associated with an increased level of apoptosis in a human subject with the disease, a human subject having an increased expression of Casp12, or any combination thereof.

Methods for Preventing a Disease

Some embodiments disclosed herein provide methods for preventing a disease in an individual in need thereof, comprising identifying an individual having an increased expression level of a gene associated with the apoptosis pathway; and administering to the individual an effective amount of a nitroxide antioxidant to reduce the level of expression of the gene associated with the apoptosis pathway.

In some embodiments, the human subject is identified as having an increased expression level of a gene, such as a gene associated with the apoptosis pathway. In some embodiments, the increased expression level of the gene can be in comparison to a normal expression level. A "normal expression level" as used herein can refer to an expression level of the gene observed in a reference cell, tissue, organ or individual. For example, "normal expression level" can refer to the expression level of a gene in an individual that is less than 50, 45, 40, 35, 30, 25, 20, 15 years old, or is a at an age that is between any of the two above mentioned values. In some embodiments, "normal expression level" of a gene can refer to the expression level of the gene in an individual that is free of any disease or is not at risk of developing a disease, or in a group of disease-free individuals. In some embodiments, "normal expression level" of a gene can refer to the expression level of the gene in an unaffected cell, tissue, organ of the individual being treated. In some embodiments, the increased expression level of the gene associated with the apoptosis pathway is in comparison to the normal expression level of the gene in a tissue selected from the group consisting of a skin tissue, an immune tissue, a cardiac tissue, a kidney tissue, a pancreatic tissue, and a neuronal tissue.

Non-limiting examples of diseases associated with altered level of apoptosis include cancer; breast cancer; lung cancer; kidney cancer; cancers of the ovary and uterus; cancer of the central nervous system; cancers of the head and neck; melanoma; lymphomas; leukemia; neurological disorders; neurodegenerative diseases; Alzheimer's disease; Parkinson's disease; Huntington's disease; temporal lobe epilepsy; amyotrophic lateral sclerosis; stroke; cardiovascular disorders; ischemia; heart failure; infectious diseases; bacterial infections; viral infections; autoimmune diseases; systemic lupus erythematosus; autoimmune lymphoproliferative syndrome; rheumatoid arthritis; thyroiditis and acquired immune deficiency syndrome (AIDS).

Methods for Treating an Aging Individual

Some embodiments disclosed herein provide methods for treating in an individual having or at risk of developing a disease due to aging, comprising identifying an individual over the age of 35; and administering to the individual an effective amount of a nitroxide antioxidant to reduce the level of expression of a gene associated with the apoptosis pathway.

In some embodiments, the human subject is identified based on the age of the human subject. For example, the human subject can be identified as having an age that is, is about, is at least, is greater than, 20, 25, 30, 35, 40, 45, 50, 55, 60, 65, 70, 75, 80, 85, 90, 95, 100, or a range between two of any above mentioned values. In some embodiments, the human subject is identified as being at risk of developing a disease, but showing no symptoms of the disease, such as a neurodegenerative disease, an immune system dysfunction, a cardiovascular dysfunction, muscle atrophy, an intestinal disorder, a kidney disease, an autoimmune disease, acquired immune deficiency syndrome (AIDS), and any combination thereof.

In some embodiments, the human subject is identified as having an increased expression level of a gene, such as a gene associated with the apoptosis pathway. In some embodiments, the increased expression level of the gene can be in comparison to a normal expression level. A "normal expression level" as used herein can refer to an expression level of the gene observed in a reference cell, tissue, organ or individual. For example, "normal expression level" can refer to the expression level of a gene in an individual that is less than 50, 45, 40, 35, 30, 25, 20, 15 years old, or is a at an age that is between any of the two above mentioned values. In some embodiments, "normal expression level" of a gene can refer to the expression level of the gene in an individual that is free of any disease or is not at risk of developing a disease, or in a group of disease-free individuals. In some embodiments, "normal expression level" of a gene can refer to the expression level of the gene in an unaffected cell, tissue, organ of the individual being treated. In some embodiments, the increased expression level of the gene associated with the apoptosis pathway is in comparison to the normal expression level of the gene in a tissue selected from the group consisting of a skin tissue, an immune tissue, a cardiac tissue, a kidney tissue, a pancreatic tissue, and a neuronal tissue.

Non-limiting examples of diseases associated with altered level of apoptosis include cancer; breast cancer; lung cancer; kidney cancer; cancers of the ovary and uterus; cancer of the central nervous system; cancers of the head and neck; melanoma; lymphomas; leukemia; neurological disorders; neurodegenerative diseases; Alzheimer's disease; Parkinson's disease; Huntington's disease; temporal lobe epilepsy; amyotrophic lateral sclerosis; stroke; cardiovascular disorders; ischemia; heart failure; infectious diseases; bacterial infections; viral infections; autoimmune diseases; systemic lupus erythematosus; autoimmune lymphoproliferative syndrome; rheumatoid arthritis; thyroiditis and acquired immune deficiency syndrome (AIDS).

Methods for Preventing or Ameliorating the Progression of a Disease

Some embodiments disclosed herein provide methods for treating, ameliorating, preventing or inhibiting the progression of a disease associated with an increased level of apoptosis in an individual in need thereof, comprising identifying an individual affected by or at risk of developing a disease associated with an increased level of apoptosis; and administering to the individual an effective amount of a nitroxide antioxidant to reduce the level of expression of a gene associated with the apoptosis pathway. In some embodiments, the expression level of the gene associated with the apoptosis pathway in a neuronal cell is reduced. In some embodiments, the disease associated with an increased level of apoptosis may be selected from the group consisting of a neurodegenerative disease, an immune system dysfunction, a cardiovascular dysfunction, muscle atrophy, an intestinal disorder, a kidney disease, an autoimmune disease, acquired immune deficiency syndrome (AIDS), and any combination thereof. In some embodiments, the methods comprise determining the expression level of one or more genes associated with the apoptosis pathway. However, this may not be necessary in some instances, such as where an increased expression level of one or more genes associated with the apoptosis pathway can be inferred from the human subject's age, family history, health conditions, medical history, habits, or a combination thereof. In some embodiments, the methods disclosed herein may be used to treat a human subject shows no symptoms of a disease associated with an increased apoptosis, but is at risk of having a disease associated with an increased apoptosis. Exemplary risk factors for a disease associated with an increased apoptosis include, but are not limited to, age, family history, health conditions, medical history, habits, or a combination thereof.

In some embodiments, administering to the human subject an effective amount of the nitroxide antioxidant results in a reduced expression level of a gene, for example a gene associated with the apoptosis pathway. The gene associated with the apoptosis pathway can be Bak1, Pdcd5, Casp2, Tradd, Tp53inp1, Casp3, or Casp12. The treatment of the human subject with the effective amount of the nitroxide antioxidant can result in a reduced expression level of the gene. For example, the treatment can reduce the expression levels of Bak1, Pdcd5, Casp2, Tradd, Tp53inp1, Casp3, Casp12, or any combination thereof. The reduced expression of the gene counteracts the increase in the expression level of the gene or the increased level of apoptosis.

Non-limiting examples of diseases associated with increased level of apoptosis includes neurodegenerative diseases, Alzheimer's disease, Parkinson's disease, Huntington's disease, amyotrophic lateral sclerosis (ALS), temporal lobe epilepsy, stroke, heart diseases, ischemia reperfusion, chronic heart failure, bacterial infections, *Mycobacterium tuberculosis* infection, *Pseudomonas aeruginosa* infection, Chlamydiae infection, infection of enteric pathogens producing Shiga toxins, *Helicobacter pylori* infection, *Staphylococcus aureus* infection, *Streptococcus pneumoniae* infection, *Bacillus anthracis* infection, *Listeria monocytogenes* infection, *Clostridium difficile* infection, viral infections, Herpesviridae infection, Cytomegalovirus infection, hepatitis B virus infection, hepatitis C virus infection, influenza A virus infection, human immunodeficiency virus (HIV) infection and autoimmune diseases.

In some embodiments, the levels of Bak1, Pdcd5, Casp2, Tradd, Tp53inp1, Casp3, or Casp12, or any combination thereof in the connective tissue, muscle tissue, nervous tissue, or epithelial tissue may change after the nitroxide antioxidant is administered. Non-limiting examples of the connective tissue include dense connective tissue, loose connective tissue, reticular connective tissue, adipose tissue, cartilage, bone, and extracellular matrix. Non-limiting examples of the muscle tissue includes smooth muscle tissue, cardiac muscle tissue, and skeletal muscle tissue. Non-limiting examples of the nervous tissue include neural tissue of the central nervous system, neural tissue of the peripheral nervous system, the brain, spinal cord, cranial nerves, spinal nerves, and motor neurons. Non-limiting examples of the epithelial tissue include squamous epithelium, cuboidal epithelium, columnar epithelium, glandular epithelium, ciliated epithelium, and skin.

Methods for Increasing the Level of Immune Response to a Bacterial Infection

Some embodiments disclosed herein provide methods for increasing or restoring the level of immune response to a bacterial infection in an individual in need thereof, comprising identifying an individual having or at risk of developing a decreased level of immune response to a bacterial infection; and administering to the individual an effective amount of a nitroxide antioxidant to reduce the level of expression of a gene associated with the apoptosis pathway. In some embodiments, the expression level of the gene associated with the apoptosis pathway in a leukocyte is reduced. In some embodiments, the individual may be in need of a reduced expression level of the gene associated with the apoptosis pathway.

In some embodiments, administering to the human subject an effective amount of the nitroxide antioxidant results in a reduced expression level of a gene, for example a gene associated with the apoptosis pathway. The gene associated with the apoptosis pathway can be Bak1, Pdcd5, Casp2, Tradd, Tp53inp1, Casp3, or Casp12. The treatment of the human subject with the effective amount of the nitroxide antioxidant can result in a reduced expression level of the gene. For example, the treatment can reduce the expression levels of Bak1, Pdcd5, Casp2, Tradd, Tp53inp1, Casp3, Casp12, or any combination thereof. The reduced expression of the gene can result in the increased level of immune response to a bacterial infection.

Non-limiting examples of bacterial infections include *Acinetobacter* infections (*Acinetobacter baumannii*), Actinomycosis (*Actinomyces israelii, Actinomyces gerencseriae* and *Propionibacterium propionicus*), Acute enteritis (*Campylobacter jejuni*), Anthrax (*Bacillus anthracis*), Botulism (*Clostridium botulinum*), Brucellosis (*Brucella* genus), Cat-scratch disease (*Bartonella henselae*), Cellulitis (*Streptococcus* and *Staphylococcus*), Chancroid (*Haemophilus ducreyi*), Chlamydia (*Chlamydia trachomatis*), Cholera (*Vibrio cholerae*), *Clostridium perfringens* infection (*Clostridium perfringens*), Diphtheria (*Corynebacterium diphtheriae*), Typhus (*Rickettsia prowazekii*), Gonorrhea (*Neisseria gonorrhoeae*), Hansen's disease (*Mycobacterium leprae* and *Mycobacterium lepromatosis*), Leptospirosis (*Leptospira* genus), Legionnaire's Disease (*Legionella pneumophila*), Listeriosis (*Listeria monocytogenes*), Lyme borreliosis (*Borrelia burgdorferi* and other *Borrelia* species), Meningitis (*Streptococcus pneumoniae, Neisseria meningitidis, Haemophilus influenzae* and *Listeria monocytogenes*), Mycetoma (Actinomycetoma and Eumycetoma), *Mycoplasma* pneumonia (*Mycoplasma pneumoniae*), Peptic ulcer (*Helicobacter pylori*), Pertussis (*Bordetella pertussis*), Plague (*Yersinia pestis*), Pneumonia (*Diplococcus pneumoniae*), *Pseudomonas* infection (*Pseudomonas aeruginosa*), Salmonellosis (*Salmonella typhimurium* and other *Salmonella* species), Scarlatina (*Streptococcus pyogenes*), Shigellosis (*Shigella* genus), Syphilis (*Treponema pallidum*), Tetanus (*Clostridium tetani*), Trachoma (*Chlamydia trachomatis*), Tuberculosis (*Mycobacterium tuberculosis*), Tularemia (*Francisella tularensis*), Traveller's diarrhea (*Escherichia coli*), and Typhoid fever (*Salmonella typhi*).

Methods for Treating Psychiatric Conditions

Some embodiments disclosed herein provide methods for treating, ameliorating, preventing or inhibiting the progression of a psychiatric condition in an individual in need thereof, comprising identifying an individual affected by or at risk of developing a psychiatric condition; and administering to the individual an effective amount of a nitroxide antioxidant to reduce the level of expression of a gene associated with the apoptosis pathway. In some embodiments, the expression level of the gene associated with the apoptosis pathway in a neuronal cell is reduced. In some embodiments, the individual may be in need of a reduced expression level of the gene associated with the apoptosis pathway. In some embodiments, the psychiatric condition may be selected from the group consisting of schizophrenia, bipolar disease, psychotic symptoms, cognitive impairment and dementia.

In some embodiments, administering to the human subject an effective amount of the nitroxide antioxidant results in a reduced expression level of a gene, for example a gene associated with the apoptosis pathway. The gene associated with the apoptosis pathway can be Bak1, Pdcd5, Casp2, Tradd, Tp53inp1, Casp3, or Casp12. The treatment of the human subject with the effective amount of the nitroxide antioxidant can result in a reduced expression level of the gene. For example, the treatment can reduce the expression levels of Bak1, Pdcd5, Casp2, Tradd, Tp53inp1, Casp3, Casp12, or any combination thereof. The reduced expression of the gene can counteract the progression of a psychiatric condition.

Non-limiting examples of psychiatric conditions include absence epilepsy, acute stress disorder, adjustment disorder, adolescent antisocial behavior, adult antisocial behavior, agoraphobia, alcohol abuse, alcohol dependence, alcohol withdrawal, alcoholic hallucinosis, avoidant/restrictive food intake disorder, Alzheimer's disease, amnestic disorder, amphetamine dependence, anorexia nervosa, anterograde amnesia, antisocial personality disorder, attention deficit disorder, attention deficit hyperactivity disorder, autism, autophagia, avoidant personality disorder, atelophobia, Asperger syndrome, barbiturate dependence, benzodiazepine dependence, benzodiazepine misuse, benzodiazepine withdrawal, bereavement, bibliomania, binge eating disorder, bipolar disorder, bipolar I disorder, bipolar II disorder, body dysmorphic disorder, borderline intellectual functioning, borderline personality disorder, brief psychotic disorder, bulimia nervosa, caffeine-induced sleep disorder, Cannabis dependence, claustrophobia, catatonic disorder, catatonic schizophrenia, circadian rhythm sleep disorder, cocaine dependence, cocaine intoxication, cognitive disorder, communication disorder, conduct disorder, cotard delusion, cyclothymia, delirium tremens, dementia, depersonalization disorder, depressive disorder, derealization disorder, dermatillomania, desynchronosis, developmental coordination disorder, Diogenes Syndrome, dispareunia, dissociative identity disorder, dyspraxia, dyslexia, EDNOS, Ekbom's Syndrome, encopresis, epilepsy, enuresis, erotomania, exhibitionism, euphoria, factitious disorder, Fregoli delusion, fugue state, Ganser syndrome, generalized anxiety disorder, general adaptation syndrome, grandiose delusions, hallucinogen-related disorder, hallucinogen persisting perception disorder, histrionic personality disorder, Huntington's disease, hypomanic episode, hypochondriasis, insomnia, kleptomania, Korsakoffs syndrome, lacunar amnesia, major depressive disorder, major depressive episode, maladaptive daydreaming, male erectile disorder, malingering, manic episode, mathematics disorder, melancholia, minor depressive disorder, misophonia, mixed episode, mood disorder, morbid jealousy, Munchausen's syndrome, narcolepsy, narcissistic personality disorder, neurocysticercosis, nicotine withdrawal, night eating syndrome, nightmare disorder, obsessive-compulsive disorder (OCD), obsessive-compulsive personality disorder (OCPD), oneirophrenia, opioid dependence, opioid-related disorder, oppositional defiant disorder (ODD), orthorexia (ON), Ondine's curse, pain disorder, panic disorder, paranoid personality disorder, parasomnia, Parkinson's Disease, pathological gambling, perfectionism, persecutory delusion, personality disorder, phencyclidine (or phencyclidine-like)-related disorder, phobic disorder, Pica (disorder), psychosis, phonological disorder, physical abuse, polysubstance-related disorder, post-traumatic embitterment disorder (PTED), posttraumatic stress disorder (PTSD), premature ejaculation, primary hypersomnia, primary insomnia, psychogenic amnesia, psychotic disorder, pyromania, reactive attachment disorder of infancy or early childhood, recurrent brief depression, relational disorder, residual schizophrenia, retrograde amnesia, rumination syndrome, schizoaffective disorder, schizoid personality disorder, schizophrenia, schizophreniform disorder, schizotypal personality disorder, seasonal affective disorder, sedative-, hypnotic-, or anxiolytic-related disorder, selective mutism, separation anxiety disorder, severe mental retardation, shared psychotic disorder, sleep disorder, seasonal affective disorder, sleep terror disorder, sleepwalking disorder, social anxiety disorder, social phobia, somatization disorder, somatoform disorder, specific phobia, Stendhal syndrome, stereotypic movement disorder, stuttering, substance-related disorder, tardive dyskinesia, Tourette syndrome, transient tic disorder, transient global amnesia, and trichotillomania.

Methods for Counteracting Stress-Induced Apoptosis

Some embodiments disclosed herein provide methods for counteracting or preventing stress-induced apoptosis in an individual in need thereof, comprising identifying an individual affected by or at risk for stress-induced apoptosis; and administering to the individual an effective amount of a nitroxide antioxidant to reduce the level of expression of a gene associated with the apoptosis pathway. In some embodiments, the expression level of the gene associated with the apoptosis pathway is reduced in a tissue selected from the group consisting of a skin tissue, an immune tissue, a pancreatic tissue, and a neuronal tissue. In some embodiments, the individual may be in need of a reduced expression level of the gene associated with the apoptosis pathway. In some embodiments, the stress that induces apoptosis may be selected from the group consisting of UV, ethanol, heat shock and oxidative stress. In some embodiments, the stress-induced apoptosis comprises acute pancreatitis.

In some embodiments, administering to the human subject an effective amount of the nitroxide antioxidant results in a reduced expression level of a gene, for example a gene associated with the apoptosis pathway. The gene associated with the apoptosis pathway can be Bak1, Pdcd5, Casp2, Tradd, Tp53inp1, Casp3, or Casp12. The treatment of the human subject with the effective amount of the nitroxide antioxidant can result in a reduced expression level of the gene. For example, the treatment can reduce the expression levels of Bak1, Pdcd5, Casp2, Tradd, Tp53inp1, Casp3, Casp12, or any combination thereof. The reduced expression of the gene can counteract or prevent stress-induced apoptosis.

Nitroxide Antioxidant

Non-limiting examples of the nitroxide antioxidant include 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4-amino-2,2,6,6-tetramethyl-1-piperidinyloxy (Tempamine), 3-Aminomethyl-PROXYL, 3-Cyano-PROXYL, 3-Carbamoyl-PROXYL, 3-Carboxy-PROXYL, and 4-Oxo-TEMPO. TEMPO can also be substituted, typically in the 4 position, for example, 4-amino, 4-(2-bromoacetamido), 4-(ethoxyfluorophosphonyloxy), 4-hydroxy, 4-(2-iodoacetamido), 4-isothiocyanato, 4-maleimido, 4-(4-nitrobenzoyloxyl), 4-phosphonooxy, and the like.

The use of other nitroxide compounds is also contemplated. According to certain embodiments the nitroxide compound can be selected from the following formulas:

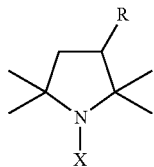

wherein X is selected from O— and OH, and R is selected from COOH, CONH, CN, and $CH_2NH_2$;

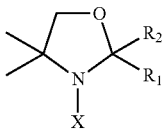

wherein X is selected from O— and OH, and $R_1$ is selected from $CH_3$ and spirocyclohexyl, and $R_2$ is selected from $C_2H_5$ and spirocyclohexyl;

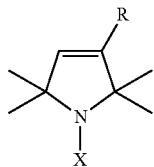

wherein X is selected from O— and OH and R is selected from CONH; and

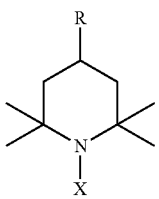

wherein X is selected from O— and OH and R is selected from H, OH, and $NH_2$.

Suitable nitroxide compounds can also be found in Proctor, U.S. Pat. No. 5,352,442, and Mitchell et al., U.S. Pat. No. 5,462,946, both of which are hereby incorporated by reference in their entireties.

Dosage

In some embodiments, the nitroxide antioxidant, non-toxic salts thereof, acid addition salts thereof or hydrates thereof may be administered systemically or locally, usually by oral or parenteral administration. The doses to be administered can be determined depending upon, for example, age, body weight, symptom, the desired therapeutic effect, the route of administration, and the duration of the treatment. In the human adult, the dose per person at a time can be generally from about 0.01 to about 1000 mg, by oral administration, up to several times per day. Specific examples of particular amounts contemplated via oral administration include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 or more mg. The dose per person at a time can be generally from about 0.01 to about 300 mg/kg via parenteral administration (preferably intravenous administration), from one to four or more times per day. Specific examples of particular amounts contemplated include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more mg/kg. Continuous intravenous administration can also contemplated for from 1 to 24 hours per day to achieve a target concentration from about 0.01 mg/L to about 100 mg/L. Non-limiting examples of particular amounts contemplated via this route include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more mg/L. The dose to be used does can depend upon various conditions, and there may be cases wherein doses lower than or greater than the ranges specified above are used.

Compositions

The nitroxide antioxidant can be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules. In such solid compositions, Tempol may be admixed with an excipient (e.g. lactose, mannitol, glucose, microcrystalline cellulose, starch), combining agents (hydroxypropyl cellulose, polyvinyl pyrrolidone or magnesium metasilicate aluminate), disintegrating agents (e.g. cellulose calcium glycolate), lubricating agents (e.g. magnesium stearate), stabilizing agents, agents to assist dissolution (e.g. glutamic acid or aspartic acid), or the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, the nitroxide antioxidant is dissolved, suspended or emulsified in a commonly used diluent (e.g. purified water, ethanol or mixture thereof). Furthermore, such liquid compositions may also comprise wetting agents or suspending agents, emulsifying agents, sweetening agents, flavoring agents, perfuming agents, preserving agents, buffer agents, or the like.

Injections for parenteral administration include solutions, suspensions, emulsions and solids which are dissolved or suspended. For injections, the nitroxide antioxidant can be dissolved, suspended and emulsified in a solvent. The solvents include, for example, distilled water for injection, physiological salt solution, vegetable oil, propylene glycol, polyethylene glycol, alcohol such as ethanol, or a mixture thereof. Moreover the injections can also include stabilizing agents, agents to assist dissolution (e.g. glutamic acid, aspartic acid or POLYSORBATE80™), suspending agents, emulsifying agents, soothing agents, buffer agents, preserving agents, etc. They can be sterilized in the final process or manufactured and prepared by sterile procedure. They can also be manufactured in the form of sterile solid compositions, such as a freeze-dried composition, and they may be sterilized or dissolved immediately before use in sterile distilled water for injection or some other solvent.

Other compositions for parenteral administration include liquids for external use, and ointment, endermic liniments, inhale, spray, suppositories for rectal administration and pessaries for vaginal administration which comprise the nixtroxide antioxidant and are administered by methods known in the art.

Spray compositions can comprise additional substances other than diluents: e.g. stabilizing agents (e.g. sodium sulfite hydride), isotonic buffers (e.g. sodium chloride, sodium citrate or citric acid). A small aerosol particle size useful for effective distribution of the medicament can be obtained by employing self-propelling compositions containing the drugs in micronized form dispersed in a propellant composition. Effective dispersion of the finely divided drug particles can be accomplished with the use of very small quantities of a suspending agent, present as a coating on the micronized drug particles. Evaporation of the propellant from the aerosol particles after spraying from the aerosol container leaves finely divided drug particles coated with a fine film of the suspending agent. In the micronized form, the average particle size can be less than about 5 microns. The propellant composition may employ, as the suspending agent, a fatty alcohol such as oleyl alcohol. The minimum quantity of suspending agent can be approximately 0.1 to 0.2 percent by weight of the total composition. The amount of suspending agent can be less than about 4 percent by weight of the total composition to maintain an upper particle size limit of less than 10 microns or 5 microns. Propellants that may be employed include hydrofluoroalkane propellants and chlorofluorocarbon propellants. Dry powder inhalation may also be employed.

Examples

The following examples are offered to illustrate but not to limit the invention.

In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1. Effects of Tempol on Expression of Genes Associated with the Apoptosis Pathway To assess the effects of Tempol on gene expression, Tempol was administered to experimental mice at a dose of 5 mg/g of food from 14 months to 31 months after birth. Mice receiving the same food without the addition of Tempol were used as a negative control. At the age of 31 months, the experimental animals were sacrificed and the hearts were surgically removed. The expression of a broad spectrum of genes in the cardiac tissue was assessed using chip-based microarray technology. Such chips are well known in the art and are widely used to assess gene expression. The experimental results showed that seven genes associated with the apoptosis pathway, Bak1, Pdcd5, Casp2, Tradd, Trp53inp1 (mouse gene of Tp53inp1), Casp3, Casp12, exhibited statistically significant decrease in expression. This result is shown in Table 1.

TABLE 1

Genes Associated With The Apoptosis Pathway Exhibiting Decreased Expression In Cardiac Tissue After Tempol Administration

| Symbol | Gene title | Control mice | Tempol-treated mice | Fold change | P-value |
|---|---|---|---|---|---|
| Bak1 | BCL2-antagonist/killer 1 | 260 | 226 | −1.15 | 0.01 |
| Pdcd5 | Programmed cell death 5 | 2863 | 2503 | −1.15 | 0.03 |
| Casp2 | Caspase 2 | 316 | 261 | −1.20 | 0.03 |
| Tradd | TNFRSF1A-associated via death domain | 288 | 233 | −1.23 | 0.01 |
| Trp53inp1 | Transformation related protein 53 inducible nuclear protein 1 | 1107 | 830 | −1.33 | 0.00 |
| Casp3 | Caspase 3, apoptosis related cysteine protease | 604 | 414 | −1.47 | 0.00 |
| Casp12 | Caspase 12 | 701 | 436 | −1.61 | 0.02 |

Example 2. Treating a Human Subject with Increased Gene Expression

A 70-kilogram human subject is identified for increased expression level of Bak1, Pdcd5, Casp2, Tradd, Trp53inp1 (mouse gene of Tp53inp1), Casp3, or Casp12. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Bak1, Pdcd5, Casp2, Tradd, Trp53inp1 (mouse gene of Tp53inp1), Casp3, or Casp12, is reduced.

Example 3. Treating a Human Subject with Decreased Immune Response to a Bacterial Infection A 70-kilogram human subject is identified for decreased immune response to a bacterial infection. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Bak1, Pdcd5, Casp2, Tradd, Trp53inp1 (mouse gene of Tp53inp1), Casp3, or Casp12, is reduced.

Example 4. Treating, Ameliorating, Preventing or Inhibiting the Progression of a Psychiatric Condition in an Individual A 70-kilogram human subject is identified as at risk for a psychiatric condition. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Bak1, Pdcd5, Casp2, Tradd, Trp53inp1 (mouse gene of Tp53inp1), Casp3, or Casp12, is reduced.

Example 5. Counteracting or Preventing Stress-Induced Apoptosis

A 70-kilogram human subject is identified as risk for stress-induced apoptosis. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Bak1, Pdcd5, Casp2, Tradd, Trp53inp1 (mouse gene of Tp53inp1), Casp3, or Casp12, is reduced.

Example 6. Preventing a Disease Associated with an Increased Level of Apoptosis A 70-kilogram human subject is identified as at risk for a disease associated with an increased level of apoptosis. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Bak1, Pdcd5, Casp2, Tradd, Trp53inp1 (mouse gene of Tp53inp1), Casp3, or Casp12, is reduced.

Example 7. Preventing a Disease Associated with an Increased Expression Level of a Gene A 70-kilogram human subject is identified as at risk of a disease having an increased expression level of Bak1, Pdcd5, Casp2, Tradd, Trp53inp1 (mouse gene of Tp53inp1), Casp3, or Casp12. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Bak1, Pdcd5, Casp2, Tradd, Trp53inp1 (mouse gene of Tp53inp1), Casp3, or Casp12, is reduced.

Example 8. Preventing a Disease Due to Aging

A 70-kilogram human subject is identified as at risk of Parkinson's disease having an age of 65. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Bak1, Pdcd5, Casp2, Tradd, Trp53inp1 (mouse gene of Tp53inp1), Casp3, or Casp12, is reduced.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for decreasing the expression level of a gene in a human subject in need thereof, comprising:
    identifying a human subject having an increased expression level of a gene associated with a disease, wherein the gene associated with the disease is selected from the group consisting of Bak1, Pdcd5, Casp2, Tradd, Tp53inp1 and Casp12; and
    administering to the human subject an effective amount of a nitroxide antioxidant to reduce the level of expression of the gene associated with the disease, wherein the nitroxide antioxidant is 4-hydroxy-2,2,6,6-tetramethyl-piperidine-1-oxyl.

2. The method of claim 1, whereby the expression level of the gene associated with the disease is reduced in the human subject.

3. The method of claim 1, whereby the expression level of the gene associated with the disease is reduced in a tissue of the human subject selected from the group consisting of a skin tissue, an immune tissue, a pancreatic tissue, and a neuronal tissue.

4. The method of claim 1, wherein the human subject is over the age of 35 or over the age of 55.

5. The method of claim 1, wherein the gene associated with the disease is Pdcd5 or Casp2.

6. The method of claim 1, wherein the gene associated with the disease is Casp2 or Tradd.

7. The method of claim 1, wherein the gene associated with the disease is Tradd or Pdcd5.

8. A method for decreasing the expression level of a gene in a human subject in need thereof, comprising:
    administering to a human subject, at risk of a disease associated with an increased expression of a gene, an effective amount of a nitroxide antioxidant to reduce the level of expression of the gene associated with the disease, wherein the gene is selected from Pdcd5, Casp2, and Tradd, wherein the nitroxide antioxidant is 4-hydroxy- 2,2,6,6-tetramethylpiperidine-1-oxyl.

9. The method of claim 8, whereby the expression level of the gene associated with the disease is reduced in the human subject.

10. The method of claim 8, whereby the expression level of the gene associated with the disease is reduced in a tissue of the human subject selected from the group consisting of a skin tissue, an immune tissue, a pancreatic tissue, and a neuronal tissue.

11. The method of claim 8, wherein the human subject is over the age of 35.

12. The method of claim 8, wherein the human subject is over the age of 55.

13. The method of claim 8, wherein the gene associated with the disease is Pdcd5.

14. The method of claim 8, wherein the gene associated with the disease is Casp2.

15. The method of claim 8, wherein the gene associated with the disease is Tradd.

16. A method for decreasing the expression level of a gene in a human subject in need thereof, comprising:
    administering to a human subject, known to have an increased expression of a gene associated with a disease, an effective amount of a nitroxide antioxidant to reduce the level of expression of the gene associated with the disease, wherein the gene associated with the disease is selected from Bak1, Tp53inp1, and Casp12, wherein the nitroxide antioxidant is 4-hydroxy-2,2,6,6-tetramethylpiperidine-1-oxyl.

17. The method of claim 16, whereby the expression level of the gene associated with the disease is reduced in the human subject.

18. The method of claim 16, whereby the expression level of the gene associated with the disease is reduced in a tissue of the human subject selected from the group consisting of a skin tissue, an immune tissue, a pancreatic tissue, and a neuronal tissue.

19. The method of claim 16, wherein the human subject is over the age of 35 or over the age of 55.

20. The method of claim 16, wherein the gene associated with the disease is Bak1 or Tp53inp1.

21. The method of claim 16, wherein the gene associated with the disease is Tp53inp1 or Casp12.

22. The method of claim 16, wherein the gene associated with the disease is Bak1 or Casp12.

23. A method for decreasing the expression level of a gene in a human subject in need thereof, comprising:
    administering to a human subject, at risk of a disease associated with an increased expression of a gene, an effective amount of a nitroxide antioxidant to reduce the level of expression of the gene associated with the disease, wherein the gene is selected from Bak1, Tp53inp1, and Casp12, wherein the nitroxide antioxidant is 4-hydroxy-2,2,6,6-tetramethylpiperidine-1-oxyl.

24. The method of claim 23, whereby the expression level of the gene associated with the disease is reduced in the human subject.

25. The method of claim 23, whereby the expression level of the gene associated with the disease is reduced in a tissue of the human subject selected from the group consisting of a skin tissue, an immune tissue, a pancreatic tissue, and a neuronal tissue.

26. The method of claim 23, wherein the human subject is over the age of 35.

27. The method of claim 23, wherein the human subject is over the age of 55.

28. The method of claim 23, wherein the gene associated with the disease is Bak1.

29. The method of claim 23, wherein the gene associated with the disease is Tp53inp1.

30. The method of claim 23, wherein the gene associated with the disease is Casp12.

* * * * *